(12) United States Patent
Mirzadegan et al.

(10) Patent No.: US 7,388,111 B2
(45) Date of Patent: Jun. 17, 2008

(54) NON-NUCLEOSIDE REVERSE TRANSCRIPTASE INHIBITORS

(75) Inventors: Taraneh Mirzadegan, Los Altos, CA (US); Tania Silva, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 66 days.

(21) Appl. No.: 11/583,346

(22) Filed: Oct. 18, 2006

(65) Prior Publication Data

US 2007/0088053 A1    Apr. 19, 2007

Related U.S. Application Data

(60) Provisional application No. 60/728,443, filed on Oct. 19, 2005.

(51) Int. Cl.
*C07C 233/01*    (2006.01)
*A01N 37/18*    (2006.01)

(52) U.S. Cl. ........................ 564/174; 514/617; 514/622

(58) Field of Classification Search ...................... None
See application file for complete search history.

(56) References Cited

U.S. PATENT DOCUMENTS

| 6,028,080 | A | 2/2000 | Ackermann et al. |
| 6,710,205 | B2 | 3/2004 | Tani et al. |
| 2003/0114435 | A1 | 6/2003 | Tani et al. |
| 2003/0187068 | A1 | 10/2003 | Miyachi et al. |
| 2003/0220241 | A1 | 11/2003 | Defeo-Jones et al. |
| 2008/0020981 | A1* | 1/2008 | Sweeney ..................... 514/12 |

FOREIGN PATENT DOCUMENTS

| WO | WO 93/15043 A1 | 8/1993 |
| WO | WO 96/22990 A2 | 8/1996 |
| WO | WO 96/22990 A3 | 8/1996 |
| WO | WO 97/26244 A1 | 7/1997 |
| WO | WO 98/50346 A2 | 11/1998 |
| WO | WO 98/50346 A3 | 11/1998 |
| WO | WO 99/17777 A1 | 4/1999 |
| WO | WO 99/55663 A1 | 11/1999 |
| WO | WO 99/65874 A1 | 12/1999 |
| WO | WO 00/64876 A1 | 11/2000 |
| WO | WO 01/17982 A1 | 3/2001 |
| WO | WO 01/19788 A2 | 3/2001 |
| WO | WO 01/19788 A3 | 3/2001 |
| WO | WO 01/21596 A1 | 3/2001 |
| WO | WO 01/64642 A2 | 9/2001 |
| WO | WO 01/64642 A3 | 9/2001 |
| WO | WO 02/057236 A1 | 7/2002 |
| WO | WO 02/070494 A1 | 9/2002 |
| WO | WO 2005/102989 A1 | 11/2005 |

OTHER PUBLICATIONS

W. Buckheit, Jr., Non-nucleoside reverse transcriptase inhibitors: perspectives for novel therapeutic compounds and strategies for treatment of HIV infection, *Expert Opin. Investig.* Drugs 2001 10(8):1423-1442.
R. W. Carling et al., 4-Substituted-3-phenylquinolin-2(1H)-ones: Acidic and Nonacidic Glycine Site N-Methyl-D-aspartate Antagonists with in Vivo Activity, *J. Med. Chem.*, 1997 40:754-765.
J. H. Chan et al., Novel Benzophenones as Non-nucleoside Reverse Transciptase Inhibitors of HIV-1, *J. Med Chem.* 2004 47(5):1175-1182.
E. De. Clercq, New Developments in Anti-HIV Chemotherap. *Curr. Med. Chem.* 2001 8:1543-1572.
M. C. Iles et al., Carbonic Anhydrase Inhibitors. Inhibition of Tumor-Associated Isozyme IX by Halogensulfanilamide and Halogenophenylaminobenzolamide Derivatives, *J. Med. Chem.* 2003 46(11):2187-2196.
A. Kreimeyer et al., Evaluation and Biological Properties of Reactive Ligands for the Mapping of the Glycine Site on the N-Methyl-D-aspartate (NMDA) Receptor, *J. Med. Chem.* 1999 42:4394-4404.
J. J. Kulagowski et al., 3'-(Arylmethyl)- and 3'-(Aryloxy)-3-phenyl-4-hydroxyquinolin- 2(1H)-ones: Orally Active Antagonists of the Glycine Site on the NMDA Receptor, *J. Med. Chem.* 1994 37:1402-1405.
M. Rowley et al., Effect of Plasma Protein Binding on in Vivo Activity and Brain Penetration of Glycine/NMDA Receptor Antagonists, *J. Med. Chem.* 1997 40:4053-4068.
P.G. Wyatt et al., Benzophenone Derivatives: A Novel Series of Potent and Selective Inhibitors of Human Immunodeficiency Virus Type 1 Reverse Transcriptase, *J. Med. Chem.* 1995 38(10):1657-1665).

* cited by examiner

*Primary Examiner*—Yvonne Eyler
*Assistant Examiner*—Yevegeny Valenrod
(74) *Attorney, Agent, or Firm*—Brian L. Buckwalter

(57) ABSTRACT

The present invention provides for compounds useful for treating an HIV-1 infection, or preventing an HIV-1 infection, or treating AIDS or ARC. The compounds of the invention are of formula I wherein R1-R4 and Ar are as herein defined. Also disclosed in the present invention are methods of treating an HIV-1 infection with compounds defined herein and pharmaceutical compositions containing said compounds

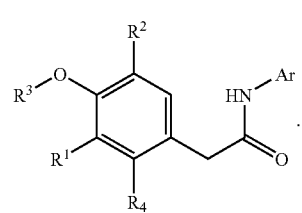

(1)

15 Claims, No Drawings

NON-NUCLEOSIDE REVERSE TRANSCRIPTASE INHIBITORS

CROSS REFERENCE TO PRIOR APPLICATIONS

This application claims the benefit of priority to U.S. Ser. No. 60/728,443 filed Oct. 19, 2005 the contents of which are hereby incorporated in their entirety by reference.

FIELD OF THE INVENTION

The invention relates to the field of antiviral therapy and, in particular, to non-nucleoside compounds that inhibit HIV-1 reverse transcriptase and are useful for treating Human Immunodeficiency Virus (HIV-1) mediated diseases. The invention provides novel N-phenyl phenylacetamide compounds according to formula I, for treatment or prophylaxis of HIV-1 mediated diseases, AIDS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the CD4$^+$ T-cell, with attendant susceptibility to opportunistic infections. HIV infection is also associated with AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV-1 by inhibition of virally encoded enzymes.

Some currently available chemotherapy targets two crucial viral enzymes: HIV protease and HIV reverse transcriptase. (J. S. G. Montaner et al. *Antiretroviral therapy: 'the state of the art'*, Biomed. & Pharmacother. 1999 53:63-72; R. W. Shafer and D. A. Vuitton, *Highly active retroviral therapy (HAART) for the treatment of infection with human immunodeficiency virus type*, Biomed. & Pharmacother. 1999 53 :73-86; E. De Clercq, *New Developments in Anti-HIV Chemotherap.* Curr. Med. Chem. 2001 8:1543-1572). Two general classes of RTI inhibitors have been identified: nucleoside reverse transcriptase inhibitors (NRTI) and non-nucleoside reverse transcriptase inhibitors.

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV-1 reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq *The role of non-nucleoside reverse transcriptase inhibitors (NNRTIs) in the therapy of HIV infection*, Antiviral Res. 1998 38:153-179; E. De Clercq *New Developments in Anti-HIV Chemotherapy*, Current Med. Chem. 2001 8(13):1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only three compounds have been approved for HIV-1 therapy: efavirenz, nevirapine and delavirdine.

Initially viewed as a promising class of compounds, in vitro and in vivo studies quickly revealed the NNRTIs presented a low barrier to the emergence of drug resistant HIV-1 strains and class-specific toxicity. Drug resistance frequently develops with only a single point mutation in the wild type RT. While combination therapy with NRTIs, PIs and NNRTIs has, in many cases, dramatically lowered viral loads and slowed disease progression, significant therapeutic problems remain. (R. M. Gulick, Eur. Soc. Clin. Microbiol. and Inf. Dis. 2003 9(3):186-193) The cocktails are not effective in all patients, potentially severe adverse reactions often occur and the rapidly reproducing HIV-1 virus has proven adroit at creating mutant drug-resistant variants of wild type protease and reverse transcriptase. There remains a need for safer drugs with activity against wild type and commonly occurring resistant strains of HIV-1.

2-Benzoyl phenyl-N-[phenyl]-acetamide compounds 2a and 2b have been shown to inhibit HIV-1 reverse transcriptase (P. G. Wyatt et al., J. Med. Chem. 1995 38(10): 1657-1665). Further screening identified related compounds, e.g. 2-benzoyl phenyloxy-N-[phenyl]-acetamide, 3a, and a sulfonamide derivative 3b which also inhibited reverse transcriptase (J. H. Chan et al., J. Med. Chem. 2004 47(5):1175-1182; C. L. Webster et al., WO01/17982).

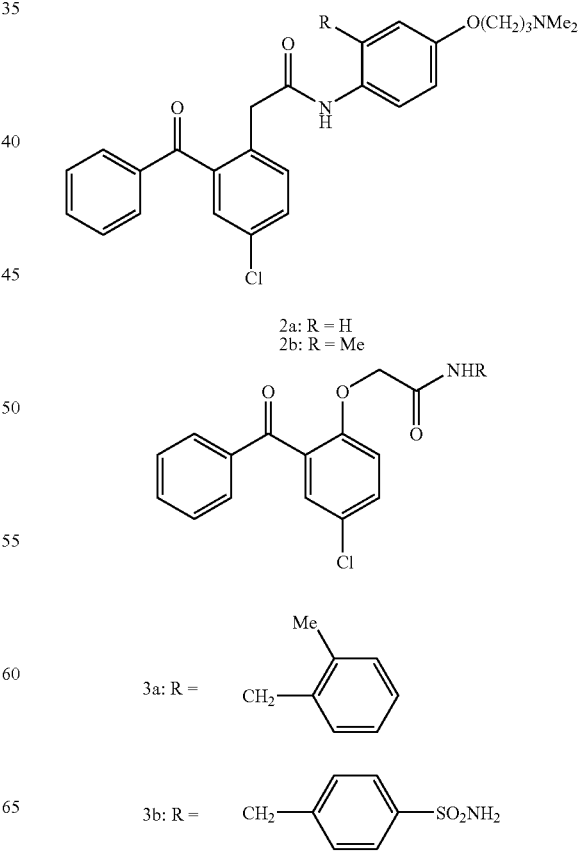

Pyridazinone non-nucleoside reverse transcriptase inhibitors 1 have been described by J. P. Dunn et al. in U. S. Publication 20040198736 filed Mar. 23, 2004 and by J. P. Dunn et al. in U.S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors 2 have been disclosed by J. P. Dunn et al. in U.S. Publication No. 20040192704 filed Mar. 23, 2004 and by J. P. Dunn et al. in U.S. Publication No. 20060025462 filed Jun. 27, 2005. Related compounds are disclosed by Y. D. Saito et al. in U.S. Ser. No. 60/722,335. Phenylacetamide non-nucleoside reverse transcriptase inhibitors have been disclosed by J. P. Dunn et al. in U.S. Ser. No. 11/112,591 filed Apr. 22, 2005 and methods for treating retroviral infection with phenylacetamide compounds have been disclosed by J. P. Dunn et al. in U.S. Publication No. 20050239881 filed Apr. 22, 2005; T. Mirzadegan and T. Silva in U.S. Ser. No. 60/728,443 filed Oct. 19, 2005; and Z. K. Sweeney and T. Silva in U.S. Ser. No 60/728,609 filed Oct. 19, 2005. These applications are hereby incorporated by reference in their entirety.

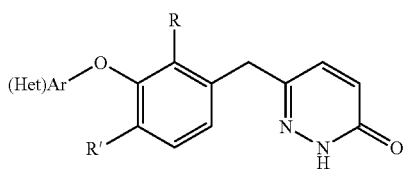

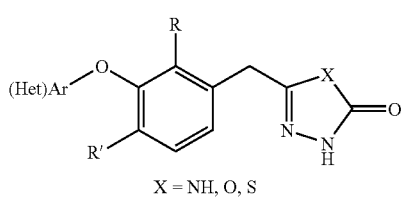

X = NH, O, S

In WO2006/067587 published Jun. 26, 2006, L. H. Jones et al. disclose biaryl ether derivatives of formula 6 and compositions containing them which bind to the enzyme reverse transcriptase and are modulators, especially inhibitors, thereof.

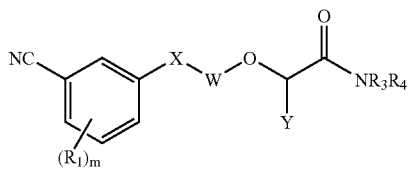

(6)

SUMMARY OF THE INVENTION

The present invention relates to compounds of formula I

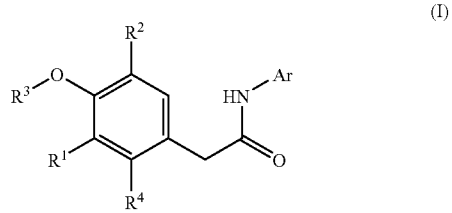

(I)

wherein:
$R^1$ is halogen, $C_{1-6}$ alkyl, $C_{1-6}$ alkoxy, nitro or amino;
$R^2$ is hydrogen or fluorine
$R^3$ is phenyl substituted with one to three substituents independently selected from the group consisting of $C_{1-6}$ alkyl, $C_{1-6}$ haloalkyl, $C_{3-8}$ cycloalkyl, halogen, cyano and nitro;
$R^4$ is hydrogen, $C_{1-6}$ alkyl or halogen;
Ar is a substituted phenyl ring according to formula IIa with the proviso that $R^{7a}$ and $R^{7c}$ are not both hydrogen or if $R^{7c}$ is hydrogen then $R^{7a}$ is halogen, $C_{1-6}$ haloalkyl, $C_{1-6}$ alkoxy, cyano or $C_{1-6}$ alkyl wherein:

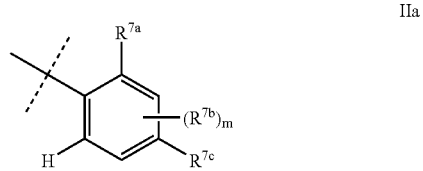

IIa $R^{7a}$ is selected from the group consisting of hydrogen, $C_{1-6}$ alkyl, $C_{1-3}$ haloalkyl, $C_{3-7}$ cycloalkyl, $C_{1-6}$ alkoxy, $C_{1-6}$ haloalkoxy, halogen and cyano;
$R^{7c}$ is selected from the group consisting of hydrogen, —S(O)$_2$NR$^8$R$^9$, —X$^2$CH$_2$(CH$_2$)$_p$S(O)$_2$NR$^8$R$^9$; —X$^4$(CH$_2$)$_v$COOR$^{10}$, —X$^4$(CH$_2$)$_v$CN, —OR$^{13}$, —CO$_2$R$^{11}$, —CN, —CONR$^{8a}$R$^{9a}$ and X$^4$(CH$_2$)$_v$CONR$^{8a}$R$^{9a}$;
$R^{7b}$ in each incidence is independently selected from the group consisting of $C_{1-6}$ alkyl; $C_{1-6}$ haloalkyl, $C_{1-6}$ alkoxy, $C_{1-6}$ alkylthio, $C_{1-6}$ alkylsulfinyl, $C_{1-6}$ sulfonyl, amino $C_{1-6}$ alkylsulfonyl, SO$_2$NR$^{11a}$R$^{11b}$, $C_{1-6}$ haloalkoxy, $C_{1-6}$ haloalkylthio, halogen, hydroxy, amino, $C_{1-6}$ alkylamino, $C_{1-6}$ dialkylamino, aminoacyl, acyl, CONR$^8$R$^9$, nitro, cyano and $C_{1-6}$ heteroalkoxy;
$R^8$ and $R^9$ (i) taken independently, one of $R^8$ and $R^9$ is hydrogen or $C_{1-6}$ alkyl and the other of $R^8$ and $R^9$ is selected from the group consisting of hydrogen, $C_{1-6}$ alkyl, —C(=O)R$^{12}$, —(CH$_2$)$_2$N[(CH$_2$)$_2$]$_2$X$^3$ or —(CH$_2$)$_2$NR$^{11a}$R$^{11b}$; or, (ii) R$^8$ and R$^9$ taken together are (CH$_2$)$_2$—X$^3$—(CH$_2$)$_2$ or —(CH$_2$)$_o$— wherein the —(CH$_2$)$_o$— moiety is optionally substituted with one or two substituents selected from the group consisting of halogen, hydroxyl and NR$^{11a}$R$^{11b}$;
$R^{8a}$ and $R^{9a}$ (i) taken independently, one of $R^8$ and $R^9$ is hydrogen or $C_{1-6}$ alkyl and the other of $R^8$ and $R^9$ is selected from the group consisting of hydrogen, $C_{1-6}$ hydroxyalkyl, —(CH$_2$)$_v$N[(CH$_2$)$_2$]$_2$X$^3$ and —(CH$_2$)$_v$NR$^{11a}$R$^{11b}$ or, (ii) R$^{8a}$ and R$^{9a}$ taken together with the nitrogen to which they are attached are pyrrolidine, piperidine said pyrrolidine or said piperidine optionally substituted with a hydroxyl or (iii) $R^{8a}$ and $R^{9a}$ taken together are $(CH_2)_2$—$X^3$—$(CH_2)_2$;

$R^{10}$ is $C_{1-6}$ alkyl;
$R^{11}$ is hydrogen or $C_{1-6}$ alkyl;
$R^{11a}$ and $R^{11b}$ are independently $R^{11}$;
$R^{12}$ is $C_{1-10}$ alkyl, —$(CH_2)_sNHR^{11a}R^{11b}$, —$(CH_2)_sOR^{11}$, —$CH_2CH(OH)CH_3$, —$CH_2N[(CH_2)_2]_2O$, —$(CH_2)_2CO_2R^{11}$, optionally substituted phenyl or pyridinyl;
$R^{13}$ is hydrogen or $C_{1-6}$ alkyl;
$X^2$ is —O— or a bond;
$X^3$ is —O—, —$S(O)_n$— or $NR^{11}$;
$X^4$ is O— or —$S(O)_n$—;
m and n are independently integers from 0 to 2;
o is an integer from 4 to 6;
p is an integer from 0 to 6;
s is an integer from 1 to 2;
v is an integer from 1 to 6; and, hydrates, solvates, and pharmaceutically acceptable salts thereof.

Compounds of formula I are useful inhibitors of HIV reverse transcriptase and afford a method for prevention and treatment of HIV infections and the treatment of AIDS and/or ARC. HIV undergoes facile mutations of its genetic code resulting in strains with reduced susceptibility to therapy with current therapeutic options. The present invention also relates to compositions containing compounds of formula I useful for the prevention and treatment of HIV infections and the treatment of AIDS and/or ARC. The present invention further relates to compounds of formula I which are useful in mono- or combination therapy with other anti-viral agents.

DETAILED DESCRIPTION OF THE INVENTION

In one embodiment of the present invention there is provided a compound according to formula I wherein $R^1$, $R^2$, $R^3$, $R^4$, $R^{7a}$, $R^{7b}$, $R^{7c}$, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above. The phrase "as defined herein above" refers to the broadest definition for each group as provided in the Summary of the Invention. In other embodiments provided below, substituents present in each embodiment which are not explicitly limited within the description of an embodiment retain the broadest definition provided in the Summary of the Invention.

In one embodiment of the present invention there is provided a compound according to formula I wherein $R^4$ is hydrogen or $C_{1-6}$ alkyl; $R^{7a}$ is selected from the group consisting of hydrogen, $C_{1-6}$ alkyl, $C_{1-3}$ haloalkyl, $C_{1-6}$ alkoxy, $C_{1-6}$ haloalkoxy, halogen and cyano; $R^1$, $R^2$, $R^3$, $R^4$, $R^{7b}$, $R^{7c}$, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above.

In another embodiment of the present invention there is provided a compound according to formula I wherein $R^{7a}$ is hydrogen, $C_{1-6}$ alkyl, $C_{1-6}$ alkoxy, cyano or halogen; m=0 or m=1 and $R^{7b}$ is $C_{1-6}$ alkyl; $R^{7c}$ is selected from the group consisting of hydrogen, —$S(O)_2NR^8R^9$, —$X^2CH_2(CH_2)_pS(O)_2NR^8R^9$, —$X^4(CH_2)_vCOOR^{10}$, $X^4(CH_2)_vCONR^8R^9$, —$X^4(CH_2)_vCOOR^{10}$, —$X^4(CH_2)_vCN$, $C_{1-6}$ alkoxy, cyano and $CO_2R^{11}$ with the proviso that both $R^{7a}$ and $R^{7c}$ are not both hydrogen, and the other substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^4$ is hydrogen or $C_{1-6}$ alkyl; $R^{7a}$ is hydrogen, $C_{1-6}$ alkyl, $C_{14}$ alkoxy, cyano or halogen; M=0 or m=1 and R7b is C1-6 alkyl; $R^{7c}$ is selected from the group consisting of hydrogen, —$S(O)_2NR^8R^9$, —$X^2CH_2(CH_2)_pS(O)_2NR^8R^9$, —$X^4(CH_2)_vCOOR^{10}$, —$X^4(CH_2)_vCONR^8R^9$, —$X^4(CH_2)_vCOOR^{10}$, —$X^4(CH_2)_vCN$, $C_{1-6}$ alkoxy, cyano, —$CO_2R^{11}$ with the proviso that both $R^{7a}$ and $R^{7c}$ are not both hydrogen and the other substituents not specifically limited in this embodiment are as defined herein above.

In another embodiment of the present invention there is provided a compound according to formula I wherein $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2 NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero and the substitutents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$, and —$X^4(CH_2)_vCOOR^{10}$; both $R^8$ and $R^9$ are hydrogen; m is zero; and, the substitutents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is phenyl independently substituted in each occurrence with one to three groups selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero; and, the substitutents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a disubstituted phenyl independently substituted in each occurrence with two groups selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero; and, the substitutents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^4$ is hydrogen or $C_{1-6}$ alkyl; $R^3$ is a 3,5- or 2,5-disubstituted phenyl independently substituted in each occurrence with two selected from the group consisting of halogen, cyano, $C_{1-6}$ haloalkyl and cyclopropyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero; and, the substitutents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a 3,5- or 2,5-disubstituted phenyl independently substituted in each occurrence with two selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero; and, the substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a 2,3,5-trisubstituted phenyl independently substituted in each occurrence with three groups selected from the group consisting of halogen, cyano, $C_{1-6}$ haloalkyl and cyclopropyl; m is zero; $R^4$ is hydrogen or $C_{1-6}$ alkyl; $R^{7a}$ is hydrogen, $C_{1-6}$ alkyl or halogen; $R^{7c}$ is selected from the group consisting of —$S(O)_2NR^8R^9$, —$X^2CH_2(CH_2)_pS(O)_2NR^8R^9$ and —$X^4(CH_2)_vCOOR^{10}$; both $R^8$ and $R^9$ are hydrogen; m is zero; and, the substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is phenyl independently substituted in each occurrence with one to three groups selected from the group consisting of halogen, cyano, $C_{1-6}$ haloalkyl and cyclopropyl; m is zero; $R^4$ is hydrogen or $C_{1-6}$ alkyl; $R^{7a}$ is hydrogen, $C_{1-6}$ alkyl or halogen; $R^{7c}$ is —$S(O)_2NR^8R^9$; and, the substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is phenyl independently substituted in each occurrence with one to three groups selected from the group consisting of halogen, cyano, $C_{1-6}$ haloalkyl and cyclopropyl; m is zero; $R^4$ is hydrogen or $C_{1-6}$ alkyl; $R^{7a}$ is hydrogen, $C_{1-6}$ alkyl or halogen; $R^{7c}$ is —$S(O)_2NR^8R^9$; $R^8$ and $R^9$ are hydrogen; and, substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a 3,5-disubstituted or a 2,5-disubstituted phenyl independently substituted in each occurrence with two groups selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is —$S(O)_2NR^8R^9$; m is zero; and, the substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a 3,5-disubstituted or a 2,5-disubstituted phenyl independently substituted in each occurrence with two groups selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is —$S(O)_2NR^8R^9$; $R^8$ and $R^9$ are hydrogen; m is zero; and, the substituents not specifically limited in this embodiment are as defined herein above.

In another embodiment of the present invention there is provided a compound according to formula I wherein $R^1$ is chloro, bromo, $C_{1-6}$ alkyl or $C_{1-6}$ alkoxy; $R^2$ is hydrogen or fluoro; $R^3$ is a 2,3,5-trisubstituted phenyl independently substituted in each occurrence with three groups selected from the group consisting of halogen, cyano, $C_{1-6}$ haloalkyl and cyclopropyl; $R^4$ is hydrogen or $C_{1-6}$ alkyl; $R^{7a}$ is hydrogen, $C_{1-6}$ alkyl or halogen; $R^{7c}$ is —$S(O)_2NR^8R^9$; m is zero; and, the substituents not specifically limited in this embodiment are as defined herein above.

In another embodiment of the present invention there is provided a compound according to formula I wherein $R^{7a}$ is hydrogen, $C_{1-6}$ alkyl, $C_{1-6}$ alkoxy, cyano or halogen; M=0 or m=1 and R7b is C1-6 alkyl; $R^{7c}$ is $C(O)NR^{8a}R^{9a}$; at least one of $R^{8a}$ and $R^{9a}$ are other than hydrogen; and the other substituents not specifically limited in this embodiment are as defined herein above.

In another embodiment of the present invention there is provided a compound selected from the group consisting of I-1 to I-65 to I-66 in TABLE 1.

In another embodiment of the present invention there is provided a compound according to formula I wherein $R^{7a}$ is hydrogen, $C_{1-6}$ alkyl, $C_{1-6}$ alkoxy, cyano or halogen; M=0 or m=1 and R7b is C1-6 alkyl; $R^{7c}$ is $C(O)NR^{8a}R^{9a}$; $R^{8a}$ is hydrogen; $R^{9a}$ is —$(CH_2)_vN[(CH_2)_2]_2X^3$ or —$(CH_2)_vNR^{11a}R^{11b}$; and, the other substituents not specifically limited in this embodiment are as defined herein above.

In another embodiment of the present invention there is provided a method for treating an HIV-1 infection, or preventing an HIV-1 infection, or treating AIDS or ARC, comprising: administering to a host in need thereof a therapeutically effective amount of a compound according to formula I wherein $R^1$, $R^2$, $R^3$, $R^4$, $R^{7a}$, $R^{7b}$, $R^7c$, $R^8$, $R^9$, $R^{8a}$, $R^{9a}$, $R^{10}$, $R^{11}$, $R^{11a}$, $R^{11b}$, $R^2$, $R^3$, $X^2$, $X^3$, $X^4$, m, n, o, p, s and v are as defined herein above.

In another embodiment of the present invention there is provided a method for treating an HIV-1 infection, or preventing an HIV-1 infection, or treating AIDS or ARC, comprising: administering to a host in need thereof a therapeutically effective amount of a compound according to formula I wherein $R^{7a}$ is hydrogen, $C_{1-6}$ alkyl, $C_{1-6}$ alkoxy, cyano or halogen; M=0 or m=1 and R7b is C1-6 alkyl; $R^{7c}$ is selected from the group consisting of hydrogen, —$S(O)_2NR^8R^9$, —$X^2CH_2(CH_2)_pS(O)_2NR^8R^9$, —$X^4(CH_2)_vCOOR^{10}$, $X^4(CH_2)_vCONR^8R^9$, —$X^4(CH_2)_vCOOR^{10}$, —$X^4(CH_2)_vCN$, $C_{1-6}$ alkoxy, cyano and $CO_2R^{11}$ with the proviso that both $R^{7a}$ and $R^{7c}$ are not both hydrogen; and the other substituents not specifically limited in this embodiment are as defined herein above.

In another embodiment of the present invention there is provided a method for treating an HIV-1 infection, or preventing an HIV-1 infection, or treating AIDS or ARC, comprising: administering to a host in need thereof a therapeutically effective amount of a compound according to formula I wherein $R^{7a}$ is hydrogen, $C_{1-6}$ alkyl or halogen; $R^{7c}$ is selected from the group consisting of —$S(O)_2NR^8R^9$, $X^2_8CH_2(CH_2)_pS(O)_2NR^8R^9$ and —$X^4(CH_2)_vCOOR^{10}$; both $R^8$ and $R^9$ are hydrogen; m is zero and the substituents not specifically limited in this embodiment are as defined herein above.

In another embodiment of the present invention there is provided a method for treating an HIV-1 infection, or preventing an HIV-1 infection, or treating AIDS or ARC, comprising: co-administering to a host in need thereof a therapeutically effective amount of a compound according to formula I wherein $R^1$, $R^2$, $R^3$, $R^4$, $R^{7a}$, $R^{7b}$, $R^{7c}$, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above and at least one compound selected from the group consisting of HIV protease inhibitors, nucleoside reverse transcriptase inhibitors, non-nucleoside reverse transcriptase inhibitors, CCR5 antagonists and viral fusion inhibitors.

In another embodiment of the present invention there is provided a method for treating an HIV-1 infection, or preventing an HIV-1 infection, or treating AIDS or ARC, comprising: co-administering to a host in need thereof a therapeutically effective amount of a compound according to formula I wherein $R^1$, $R^2$, $R^3$, $R^4$, $R^{7a}$, $R^{7b}$, $R^{7c}$, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above and at least one compound selected from the group consisting zidovudine, lamivudine, didanosine, zalcitabine, stavudine, rescriptor, sustiva and viramune, efavirenz, nevirapine, delavirdine, saquinavir, ritonavir, nelfinavir, indinavir, amprenavir and lopinavir.

In another embodiment of the present invention there is provided a method for inhibiting HIV-1 reverse transcriptase comprising: administering to a host in need thereof a therapeutically effective amount of a compound according to formula I wherein $R^{7a}$ is hydrogen, $C_{1-6}$ alkyl or halogen; $R^{7c}$ is selected from the group consisting of —S(O)$_2$NR$^8$R$^9$, —X$^2$CH$_2$(CH$_2$)$_p$S(O)$_2$NR$^8$R$^9$ and —X$^4$(CH$_2$)$_v$COOR$^{10}$; both $R^8$ and $R^9$ are hydrogen; m is zero and the substituents not specifically limited in this embodiment are as defined herein above.

In another embodiment of the present invention there is provided a method for inhibiting HIV-1 reverse transcriptase comprising: administering to a host in need thereof a therapeutically effective amount of a compound according to formula I wherein $R^1$, $R^2$, $R^3$, $R^4$, $R^{7a}$, $R^{7b}$, R$^7$c, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above.

In another embodiment of the present invention there is provided a method for inhibiting HIV-1 reverse transcriptase wherein the host is infected with a strain of HIV-1 expressing a reverse transcriptase with at least one mutation compared to wild type HIV-1 comprising: administering to a host in need thereof a therapeutically effective amount of a compound according to formula I wherein $R^{7a}$ is hydrogen, $C_{1-6}$ alkyl or halogen; $R^{7c}$ is selected from the group consisting of —S(O)$_2$NR$^8$R$^9$, —X2CH$_2$(CH$_2$)$_v$S(O)$_2$NR$^8$R$^9$ and —X$^4$(CH$_2$)$_v$COOR$^{10}$; both $R^8$ and $R^9$ are hydrogen; m is zero and the substituents not specifically limited in this embodiment are as defined herein above.

In another embodiment of the present invention there is provided a method for inhibiting HIV-1 reverse transcriptase wherein the host is infected with a strain of HIV-1 expressing a reverse transcriptase with reduced susceptibility to efavirenz, nevirapine or delavirdine comprising: administering to a host in need thereof a therapeutically effective amount of a compound according to formula I wherein $R^{7a}$ is hydrogen, $C_{1-6}$ alkyl or halogen; $R^{7c}$ is selected from the group consisting of —S(O)$_2$NR$^8$R$^9$, —X$^2$CH$_2$(CH$_2$)$_p$S(O)$_2$NR$^8$R$^9$ and —X$^4$(CH$_2$)$_v$COOR$^{10}$; both $R^8$ and $R^9$ are hydrogen; m is zero and the substituents not specifically limited in this embodiment.

In another embodiment of the present invention there is provided a pharmaceutical composition for treating an HIV-1 infection, or preventing an HIV-1 infection, or treating AIDS or ARC, comprising a therapeutically effective quantity of a compound according to formula I wherein $R^1$, $R^2$, $R^3$, $R^4$, $R^{7a}$, $R^{7b}$, $R^{7c}$, $R^8$, $R^9$, $R^{8a}$, $R^{9a}$, $R^{10}$, $R^{11}$, $R^{11a}$, $R^{11b}$, $R^{12}$, $R^{13}$, $X^2$, $X^3$, $X^4$, m, n, o, p, s and v are as defined herein above admixed with at least one carrier, excipient or diluent.

In another embodiment of the present invention there is provided a pharmaceutical composition for treating an HIV-1 infection, or preventing an HIV-1 infection, or treating AIDS or ARC, comprising a therapeutically effective quantity of a compound according to formula I wherein $R^{7a}$ is hydrogen, $C_{1-6}$ alkyl or halogen; $R^{7c}$ is selected from the group consisting of —S(O)$_2$NR$^8$R$^9$, —X$^2$CH$_2$(CH$_2$)$_p$S(O)$_2$NR$^8$R$^9$ and —X$^4$(CH$_2$)$_v$COOR$^{10}$; both $R^8$ and $R^9$ are hydrogen; m is zero and the substituents not specifically limited in this embodiment are as defined herein above admixed with at least one carrier, excipient or diluent.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition for each group as provided in the Summary of the Invention.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl refers to either an aryl or a heteroaryl group.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "alkyl" as used herein denotes an unbranched or branched chain, saturated, monovalent hydrocarbon residue. "$C_{1-10}$ alkyl" as used herein refers to an alkyl composed of 1 to 10 carbons. Examples of alkyl groups include, but are not limited to, methyl, ethyl, propyl, i-propyl, n-butyl, i-butyl, t-butyl or pentyl, isopentyl, neopentyl, hexyl, heptyl, and octyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "$C_{1-10}$ alkoxy" refers to an —O-alkyl wherein alkyl is $C_{1-10}$.

The term "acyl" as used herein denotes a group of formula —C(=O)R wherein R is hydrogen or $C_{1-6}$ alkyl as defined herein. The term or "alkylcarbonyl" as used herein denotes a group of formula C(=O)R wherein R is alkyl as defined herein. The term "arylcarbonyl" as used herein means a group of formula C(=O)R wherein R is an aryl group; the term "benzoyl" as used herein an "arylcarbonyl" group wherein R is phenyl.

The term "acylamino" as used herein denotes a group of formula —NHC(=O)R wherein R is hydrogen or lower alkyl as defined herein unless defined otherwise.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)n-, RHN(CH$_2$)n-, and R$_2$N(CH$_2$)n- respectively wherein n is 1 to 6 and R is alkyl as defined above. "C$_{1-10}$ alkylamino" as used herein refers to an aminoalkyl wherein alkyl is C$_{1-10}$.

The terms "alkylsulfinyl" and "arylsulfinyl" as used herein denote a group of formula —S(=O)R wherein R is alkyl or aryl respectively and alkyl and aryl are as defined herein.

The terms "alkylsulfonyl" and "arylsulfonyl" as used herein denote a group of formula —S(=O)$_2$R wherein R is alkyl or aryl respectively and alkyl and aryl are as defined herein.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "C$_{3-7}$ cycloalkyl" as used herein refers to an cycloalkyl composed of 3 to 7 carbons in the carbocyclic ring.

The term "cyano" as used herein refers to a carbon linked to a nitrogen by a triple bond, i.e., —C≡N. The term "nitro" as used herein refers to an NO$_2$ substituent.

The term "haloalkyl" as used herein denotes a unbranched or branched chain alkyl group as defined above wherein 1, 2, 3 or more hydrogen atoms are substituted by a halogen. "C$_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "halogen" or "halo" as used herein means fluorine, chlorine, bromine, or iodine.

The term "haloalkoxy" as used herein refers to a group —OR where R is haloalkyl as defined herein. The term "haloalkylthio" as used herein refers to a group —SR where R is haloalkyl as defined herein.

The term "heteroalkoxy" as used herein means an —O-(heteroalkyl) group wherein heteroalkyl is defined herein. C$_{1-10}$ heteroalkoxy" as used herein refers to an—O-(heteroalkyl) wherein alkyl is C$_{1-10}$. Representative examples include, but are not limited to, 2-dimethylaminoethoxy and 3-sulfonamido-1-propoxy.

The terms "hydroxyalkyl" and "alkoxyalkyl" as used herein denotes unbranched or branched alkyl radical as herein defined wherein one to three hydrogen atoms on different carbon atoms is/are replaced by hydroxyl or alkoxy groups respectively.

The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_v$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, or alkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "wild type" as used herein refers to the HIV-1 virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT; RETROVIR®) from GSK; didanosine (ddI; VIDEX®) from Bristol-Myers Squibb Co. (BMS); zalcitabine (ddC; HIVID®) from Roche; stavudine (d4T; ZERIT®) from BMS; lamivudine (3TC; EPIVIR®) from GSK; abacavir (1592U89; ZIAGEN®) disclosed in WO96/30025 and available from GSK; adefovir dipivoxil (bis(POM)-PMEA; PREVON®) Gilead Sciences; lobucavir (BMS-180194), a nucleoside reverse transcriptase inhibitor disclosed in EP-0358154 and EP-0736533 and under development by BMS; BCH-10652, a reverse transcriptase inhibitor (in the form of a racemic mixture of BCH-10618 and BCH-10619) under development by Biochem Phama; emitricitabine [(−)-FTC] licensed from Emory University under Emory Univ. U.S. Pat. No. 5,814,639 and under development by Gilead Sciences, Inc; Evucitabine (β-L-D4FC; β-L-2',3'-dideoxy-5-fluoro-cytidene) licensed by Yale University to Vion Pharmaceuticals; DAPD, the purine nucleoside, (−)-β-D-2,6,-diamino-purine dioxolane disclosed in EP-0656778 and licensed by Emory University and the University of Georgia to Triangle Pharmaceuticals; and lodenosine (FddA), 9-(2, 3-dideoxy-2-fluoro-β-D-threo-pentofuranosyl)adenine, an acid stable purine-based reverse transcriptase inhibitor discovered by the NIH and under development by U.S. Bioscience Inc.

Three NNRTIs have been approved in the USA: nevirapine (BI-RG-587; VIRAMUNE®) available from Boehringer Ingelheim (BI); delaviradine (BHAP, U-90152; RESCRIPTOR®) available from Pfizer; efavirenz (DMP-266, SUSTIVA®) a benzoxazin-2-one from BMS. Other NNRTIs currently under investigation include PNU-142721, a furopyridine-thio-pyrimide under development by Pfizer; capravirine (S-1153 or AG-1549; 5-(3,5-dichlorophenyl)-thio-4-isopropyl-1-(4-pyridyl)methyl-1H-imidazol-2-ylmethyl carbonate) by Shionogi and Pfizer; emivirine [MKC-442; (1-(ethoxy-methyl)-5-(1-methylethyl)-6-(phenylmethyl)-(2,4(1H,3H)-pyrimidinedione)] by Mitsubishi Chemical Co. and Triangle Pharmaceuticals;

(+)-calanolide A (NSC-675451) and B, coumarin derivatives disclosed in NIH U.S. Pat. No. 5,489,697, licensed to Sarawak/Advanced Life Sciences; etravirine (TMC-125; 4-[6-amino-5-bromo-2-(4-cyano-phenylamino)-pyrimidin-4-yloxy]-3,5-dimethyl-benzonitrile) and DAPY (TMC120; 4-{4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin-4-yloxy)-ethyl]-5-methyl-11,12-dihydro-5H-1,5,10,12-tetraaza-dibenzo[a,e]cycloocten-6-one by Boehringer-Ingleheim; PHI-236 (7-bromo-3-[2-(2,5-dimethoxy-phenyl)-ethyl]-3,4-dihydro-1H-pyrido[1,2-a][1,3,5]triazine-2-thione) and PHI-443 (TMC-278, 1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR-from Abbott Laboratories; Lopinavir (ABT-378) also available from Abbot; KALETRA®, is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-amino acid substituted L-lysine derivatives by Procyon. Entry of HIV into target cells requires CD-4 cell surface receptor and the CCR5 (M-tropic strains) and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J. Med. Chem.* 2000 43(10):2049-2063; M. Babba et al. *Proc. Nat. Acad. Sci. USA* 1999 96:5698-5703) and TAK-220 (C. Tremblay et al. *Antimicrob. Agents Chemother.* 2005 49(8):3483-3485). WO0039125 (D. R. Armour et al.) and WO0190106 (M. Perros et al.) disclose heterocyclic compounds that are potent and selective CCR5 antagonists. Miraviroc (UK-427,857; MVC) has advanced by Pfizer to phase III clinical trials and show activity against HIV-1 isolates and laboratory strains (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4): 1268-1282; M. J. Macartney et al., 43rd *Intersci. Conf. Antimicrob. Agents Chemother.* Sep. 14-17, 2003, Abstract H-875). Schering has advanced Sch-35 1125 (SCH-C) into Phase I/II clinical studies and reported the advance of a more potent follow-up compound, Vicroviroc (Sch-417690, SCH-D) into Phase I studies. (S. W. McCrombie et al., WO00066559; B. M. Baroudy et al. WO00066558; A. Palani et al., *J. Med. Chem.* 2001 44(21): 3339-3342; J. R. Tagat et al., *J. Med. Chem.* 2001 44(21): 3343-3346; J. A. Esté, *Cur. Opin. Invest. Drugs* 2002 3(3):379-383; J. M. Struzki et al. *Proc. Nat. Acad. Sci. USA* 2001 98:12718-12723). Merck has disclosed the preparation of (2S)-2-(3-chlorophenyl)-1-N-(methyl)-N-(phenylsulfonyl)amino]-4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.*, 2001 11:265-270; P. E. Finke et al., *Bioorg. Med. Chem. Lett.*, 2001 11:2469-2475; P. E. Finke et al., *Bioorg. Med. Chem. Lett.*, 2001 11:2475-2479; J. J. Hale et al., *Bioorg. Med. Chem. Lett.*, 2001 11:2741-22745; D. Kim et al., *Bioorg. Med. Chem. Lett.*, 2001 11:3099-3102) C. L. Lynch et al. *Org. Lett.* 2003 5:2473-2475; R. S. Veazey et al. *J. Exp. Med.* 2003 198:1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J. Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published Aug. 11, 2005, S. D. Gabriel and D. M. Rotstein disclosed heterocyclic CCR5 antagonist capable of prevent HIV cell entry. In U.S. Publication No. 20060014767 published Jan. 19, 2006, E. K. Lee et al. disclosed heterocyclic CCR5 antagonist capable of prevent HIV cell entry.

Attachment Inhibitors effectively block interaction between viral envelope proteins and chemokine receptors or CD40 protein. TNX-355 is a humanized IgG4 monoclonal antibody that binds to a conformational epitope on domain 2 of CD4. (L. C. Burkly et al., *J. Immunol.* 1992 149:1779-87) TNX-355 can inhibit viral attachment of CCR5-, CXCR4- and dual/mixed tropic HIV-1 strains. (E. Godofsky et al., *In Vitro* Activity of the Humanized Anti-CD4 Monoclonal Antibody, TNX-355, against CCR5, CXCR4, and Dual-Tropic Isolates and Synergy with Enfuvirtide, 45*th Annual Interscience Conference on Antimicrobial Agents and Chemotherapy (ICAAC).* Dec. 16-19, 2005, Washington D.C. Abstract #3844; D. Norris et al. TNX-355 in Combination with Optimized Background Regime (OBR) Exhibits Greater Antiviral Activity than OBR Alone in HIV-Treatment Experienced Patients, 45*th Annual Interscience Conference on Antimicrobial Agents and Chemotherapy (ICAAC).* Dec. 16-19, 2005, Washington D.C. Abstract #4020.).

Macromolecular therapeutics including antibodies, soluble receptors and biologically active fragments thereof have become an increasingly important adjunct to conventional low molecular weight drugs. (O. H. Brekke and I. Sandlie *Nature Review Drug Discov.* 2003 2:52-62; A. M. Reichert *Nature Biotech.* 2001 19:819-821) Antibodies with high specificity and affinity can be targeted at extra-cellular proteins essential for viral cell fusion. CD4, CCR5 and CXCR4 have been targets for antibodies which inhibit viral fusion.

V. Roschke et al. (Characterization of a Panel of Novel Human Monoclonal Antibodies that Specifically Antagonize CCR5 and Block HIV-1 Entry, 44th *Annual Interscience Conference on Antimicrobial Agents and Chemotherapy* (*ICAAC*). Oct. 29, 2004, Washington D.C. Abstract #2871) have disclosed monoclonal antibodies which bind to the CCR5 receptor and inhibit HIV entry into cells expressing the CCR5 receptor. L. Wu and C. R MacKay disclose in U.S. Ser. No. 09/870,932 filed May 30, 2001 disclose monoclonal antibodies 5C7 and 2D7 which bind to the CCR5 receptor in a manner capable of inhibiting HIV infection of a cell. W. C. Olsen et al. (*J. Virol*. 1999 73(5):4145-4155) disclose monoclonal antibodies capable of inhibiting (i) HIV-1 cell entry, (ii) HIV-1 envelope-mediated membrane fusion, (iii) gp120 binding to CCR5 and (iv) CC-chemokine activity. Synergism between the anti-CCR5 antibody Pro140 and a low molecular weight CCR5 antagonists have been disclosed by Murga et al. (3rd IAS Conference on HIV Pathogenesis and Treatment, Abstract TuOa.02.06. Jul. 24-27, 2005, Rio de Janeiro, Brazil) Anti-CCR5 antibodies have been isolated which inhibit HIV-1 cell entry also have been disclosed by M. Brandt et al. in U.S. Ser. No. 11/394,439 filed Mar. 31, 2006.

FUZEON® (T-20, DP-178, pentafuside) is disclosed in U.S. Pat. No. 5,464,933. T-20 and an analog, T-1249, are analogs of HIV gp41 fragment which are effectively inhibit a conformational change required for HIV fusion. T-20 has been approved and is available from Roche and Trimeris. FUZEON is administered as a continuous sc infusion or injection in combination therapy with other classes of anti HIV drugs.

Other antiviral agents which may be useful in HIV therapy include hydroxyurea, ribavirin, IL-2, IL-12, pentafuside. Hydroxyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN® (aldesleukin) from Chiron Corp. as a lyophilized powder for fv infusion or sc administration. IL-12 is disclosed in WO96/25171 and is available from Roche and Wyeth Pharmaceuticals. Ribavirin, 1-β-D-ribofuranosyl-1H-1,2,4-triazole-3-carboxamide, is described in U.S. Pat. No. 4,211,771 and is available from ICN Pharmaceuticals.

Commonly used abbreviations include: acetyl (Ac), azo-bis-isobutyryinitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), (diphenylphosphino)ethane (dppe), (diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), acetic acid (HOAc), 1-N-hydroxybenzotriazole (HOBt), high pressure liquid chromatography (HPLC), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), 1,1'-bis-thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be recognized by one skilled in the art having referred to the disclosure contained in this Application.

The starting materials and the intermediates of the synthetic reaction schemes can be isolated and purified if desired using conventional techniques, including but not limited to, filtration, distillation, crystallization, flash column chromatography, HPLC and the like. Such materials can be characterized using conventional means, including physical constants and including, but not limited to mass spectrometry, nuclear magnetic resonance spectroscopy and infrared spectroscopy.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. One skilled in the art will be able to identify optimal reaction conditions for each transformation without undue experimentation.

While the following schemes often depict specific compounds; the reaction conditions are exemplary and can readily be adapted to other reactants. Alternative conditions also are well known. The reaction sequences in the following examples are not meant to limit the scope of the invention as set forth in the claims.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

Some structures in the following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| Cpd. No. | COMPOUND | mw | mp | HIV-RT IC$_{50}$ (μM) |
|---|---|---|---|---|
| I-1 | 2-[4-(3,5-Dicyano-phenoxy)-3-fluoro-phenyl]-N-(4-sulfamoyl-phenyl)-acetamide | 450.45 | 259.5-262.0 | 100 |
| I-2 | 2-[3-Chloro-4-(3,5-dicyano-phenoxy)-phenyl]-N-(4-sulfamoyl-phenyl)-acetamide | 466.9 | 244.5-246.7 | 10 |
| I-3 | 2-[4-(2-Bromo-5-chloro-phenoxy)-3-chloro-phenyl]-N-(4-sulfamoyl-phenyl)-acetamide | 530.23 | 221.3-223.9 | 100 |
| I-4 | 2-[4-(3,5-Dicyano-phenoxy)-3-methyl-phenyl]-N-(4-sulfamoyl-phenyl)-acetamide | 446.49 | 223.0-226.0 | 10 |
| I-5 | 2-[4-(2-Bromo-5-chloro-phenoxy)-3-chloro-phenyl]-N-[2-methyl-4-(3-sulfamoyl-propoxy)-phenyl]-acetamide | 602.33 | 191.1-193.1 | 0.1477 |
| I-6 | 2-[4-(2-Bromo-5-chloro-phenoxy)-3-chloro-phenyl]-N-(2-chloro-phenyl)-acetamide | 485.59 | 128.0-131.0 | 0.1697 |
| I-7 | 2-[4-(2-Bromo-5-chloro-phenoxy)-3-chloro-phenyl]-N-o-tolyl-acetamide | 465.17 | 158.8-162.0 | 0.8321 |
| I-8 | 2-[4-(2-Bromo-5-chloro-phenoxy)-3-chloro-phenyl]-N-(2-fluoro-phenyl)-acetamide | 469.14 | 142-143.9 | 5.81 |
| I-9 | 2-[3-Chloro-4-(3,5-dicyano-phenoxy)-phenyl]-N-(2-trifluoromethyl-phenyl)-acetamide | 455.82 | | 100 |
| I-10 | 2-[3-Chloro-4-(3,5-dicyano-phenoxy)-phenyl]-N-(4-methoxy-2-methyl-phenyl)-acetamide | 431.88 | | 100 |
| I-11 | 2-[3-Chloro-4-(3,5-dicyano-phenoxy)-phenyl]-N-(4-dimethylsulfamoyl-phenyl)-acetamide | 494.96 | | 100 |
| I-12 | 2-[3-Chloro-4-(3,5-dicyano-phenoxy)-phenyl]-N-[4-(piperidine-1-sulfonyl)-phenyl]-acetamide | 535.02 | | 100 |
| I-13 | 2-[3-Chloro-4-(3,5-dicyano-phenoxy)-phenyl]-N-[4-(morpholine-4-sulfonyl)-phenyl]-acetamide | 536.99 | | 100 |
| I-14 | 2-[3-Chloro-4-(3,5-dicyano-phenoxy)-phenyl]-N-(2,3-dimethyl-phenyl)-acetamide | 415.88 | | 100 |
| I-15 | 2-[3-Chloro-4-(3,5-dicyano-phenoxy)-phenyl]-N-(2-ethyl-phenyl)-acetamide | 415.88 | | 10 |
| I-16 | 2-[3-Chloro-4-(3,5-dicyano-phenoxy)-phenyl]-N-o-tolyl-acetamide | 401.85 | | 100 |
| I-17 | 2-[3-Chloro-4-(3,5-dicyano-phenoxy)-phenyl]-N-(2-methoxy-phenyl)-acetamide | 417.85 | | 10 |
| I-18 | 2-[4-(3-Chloro-5-cyano-phenoxy)-2,3-dimethyl-phenyl]-N-(2-chloro-4-sulfamoyl-phenyl)-acetamide new | 504.39 | 224.2-222.2 | 0.1115 |
| I-19 | 2-[3-Chloro-4-(3,5-dicyano-phenoxy)-phenyl]-N-(2-isopropyl-phenyl)-acetamide | 429.91 | | 100 |
| I-20 | N-(2-Bromo-phenyl)-2-[3-chloro-4-(3,5-dicyano-phenoxy)-phenyl]-acetamide | 466.72 | | 2.38 |
| I-21 | N-(2-Bromo-4-sulfamoyl-phenyl)-2-[3-chloro-4-(3,5-dicyano-phenoxy)-phenyl]-acetamide | 545.8 | | 0.1594 |
| I-22 | 2-[3-Chloro-4-(3,5-dicyano-phenoxy)-phenyl]-N-(4-cyano-phenyl)-acetamide | 412.84 | | 10 |

TABLE 1-continued

| Cpd. No. | COMPOUND | mw | mp | HIV-RT IC$_{50}$ (μM) |
|---|---|---|---|---|
| I-23 | 2-[4-(4-Cyano-2-methyl-phenoxy)-2,3-dimethyl-phenyl]-N-(2-methyl-4-sulfamoyl-phenyl)-acetamide | 463.56 | 242.7-243.9 | 0.2524 |
| I-24 | N-(2-Bromo-4-sulfamoyl-phenyl)-2-[4-(4-cyano-2-methyl-phenoxy)-2,3-dimethyl-phenyl]-acetamide | 528.43 | 242.5-243.6 | 0.2023 |
| I-25 | N-(2-Chloro-4-sulfamoyl-phenyl)-2-[4-(4-cyano-2-methyl-phenoxy)-2,3-dimethyl-phenyl]-acetamide | 483.97 | 239.8-240.7 | 0.1575 |
| I-26 | (4-{2-[3-Chloro-4-(3,5-dicyano-phenoxy)-phenyl]-acetylamino}-phenoxy)-acetic acid methyl ester | 475.89 |  | 100 |
| I-27 | 2-[3-Chloro-4-(3,5-dicyano-phenoxy)-phenyl]-N-(4-cyanomethoxy-phenyl)-acetamide | 442.86 |  | 100 |
| I-28 | (4-{2-[3-Chloro-4-(3,5-dicyano-phenoxy)-phenyl]-acetylamino}-phenylsulfanyl)-acetic acid methyl ester | 491.95 |  | 100 |
| I-29 | 2-[3-Chloro-4-(3,5-dicyano-phenoxy)-phenyl]-N-(2-cyano-phenyl)-acetamide | 412.84 |  | 10 |
| I-30 | 4-{2-[3-Chloro-4-(3,5-dicyano-phenoxy)-phenyl]-acetylamino}-benzoic acid methyl ester | 445.86 |  | 100 |
| I-31 | 4-{2-[3-Chloro-4-(3,5-dicyano-phenoxy)-phenyl]-acetylamino}-3-methyl-benzoic acid methyl ester | 459.89 |  | 100 |
| I-32 | 3-Chloro-4-{2-[3-chloro-4-(3,5-dicyano-phenoxy)-phenyl]-acetylamino}-benzoic acid methyl ester | 480.31 |  | 10 |
| I-33 | N-(2-Bromo-4-sulfamoyl-phenyl)-2-[4-(3-chloro-5-cyano-phenoxy)-2,3-dimethyl-phenyl]-acetamide | 548.84 | 237.0-239.7 | 0.0843 |
| I-34 | 2-[3-Chloro-4-(2-chloro-5-cyano-phenoxy)-phenyl]-N-(4-sulfamoyl-phenyl)-acetamide | 476.34 | 248.3-249.1 | 100 |
| I-35 | 2-[3-Chloro-4-(2-chloro-5-cyano-phenoxy)-phenyl]-N-(2-methyl-4-sulfamoyl-phenyl)-acetamide | 490.37 | 239.8-241.6 | 0.3946 |
| I-36 | 2-[3-Chloro-4-(2-chloro-5-cyano-phenoxy)-phenyl]-N-(2-chloro-4-sulfamoyl-phenyl)-acetamide | 510.78 | 252.9-254.2 | 0.1039 |
| I-37 | 2-[3-Chloro-4-(3-chloro-5-cyano-phenoxy)-phenyl]-N-(4-sulfamoyl-phenyl)-acetamide | 476.34 | 244.5-244.9 | 10 |
| I-38 | 2-[3-Chloro-4-(3-chloro-5-cyano-phenoxy)-phenyl]-N-(2-methyl-4-sulfamoyl-phenyl)-acetamide | 490.37 | 200.0-201.2 | 0.8063 |
| I-39 | 2-[3-Chloro-4-(3-chloro-5-cyano-phenoxy)-phenyl]-N-(2-chloro-4-sulfamoyl-phenyl)-acetamide | 510.78 | 212.8-217.6 | 0.0926 |
| I-40 | 2-[3-Chloro-4-(2,6-dichloro-phenoxy)-phenyl]-N-(4-sulfamoyl-phenyl)-acetamide | 485.77 | 237.0-237.9 | 100 |
| I-41 | 2-[3-Chloro-4-(2,6-dichloro-phenoxy)-phenyl]-N-(2-methyl-4-sulfamoyl-phenyl)-acetamide | 499.8 | 210.0-213.5 | 0.1623 |
| I-42 | 2-[3-Chloro-4-(4-cyano-2-methyl-phenoxy)-phenyl]-N-(4-sulfamoyl-phenyl)-acetamide | 455.92 | 194.9-196.4 | 100 |
| I-43 | 2-[3-Chloro-4-(4-cyano-2-methyl-phenoxy)-phenyl]-N-(2-methyl-4-sulfamoyl-phenyl)-acetamide | 469.95 | 228.2-229.8 | 0.695 |
| I-44 | 2-[3-Chloro-4-(4-cyano-2-methyl-phenoxy)-phenyl]-N-(2-chloro-4-sulfamoyl-phenyl)-acetamide | 490.37 | 209.7-211.8 | 0.0715 |
| I-45 | 2-[3-Chloro-4-(2,6-dichloro-phenoxy)-phenyl]-N-(2-chloro-4-sulfamoyl-phenyl)-acetamide | 520.22 | 223.7-225.0 | 0.0634 |
| I-46 | 2-[3-Bromo-4-(3-chloro-5-cyano-phenoxy)-phenyl]-N-(4-sulfamoyl-phenyl)-acetamide | 520.79 | 205.3-207.4 | 6 |
| I-47 | 2-[3-Bromo-4-(3-chloro-5-cyano-phenoxy)-phenyl]-N-(2-methyl-4-sulfamoyl-phenyl)-acetamide | 534.82 | 214.6-215.9 | 0.3392 |
| I-48 | 2-[3-Bromo-4-(3-chloro-5-cyano-phenoxy)-phenyl]-N-(2-chloro-4-sulfamoyl-phenyl)-acetamide | 555.24 | 205.0-207.3 | 0.0191 |
| I-49 | 2-[3-Bromo-4-(3-chloro-5-cyano-phenoxy)-phenyl]-N-(4-sulfamoylmethyl-phenyl)-acetamide | 534.82 | 133.4-135.3 | 2.35 |
| I-50 | 2-[3-Bromo-4-(3-chloro-5-cyano-phenoxy)-phenyl]-N-(2-bromo-4-sulfamoyl-phenyl)-acetamide | 599.69 | 168.1-170.4 | 0.0135 |
| I-51 | 2-[4-(3-Chloro-5-cyano-phenoxy)-3-methoxy-phenyl]-N-(2-methyl-4-sulfamoyl-phenyl)-acetamide | 485.95 | 210.6-211.9 | 1.8 |

TABLE 1-continued

| Cpd. No. | COMPOUND | mw | mp | HIV-RT IC$_{50}$ ($\mu$M) |
|---|---|---|---|---|
| I-52 | 2-[4-(3-Chloro-5-cyano-phenoxy)-3-methoxy-phenyl]-N-(2-chloro-4-sulfamoyl-phenyl)-acetamide | 506.36 | 217.0-218.2 | 0.518 |
| I-53 | N-(2-Bromo-4-sulfamoyl-phenyl)-2-[4-(3-chloro-5-cyano-phenoxy)-3-methoxy-phenyl]-acetamide | 550.82 | 204.1-206.0 | 0.3938 |
| I-54 | 2-[4-(4-Cyano-2-methyl-phenoxy)-3-methoxy-phenyl]-N-(2-methyl-4-sulfamoyl-phenyl)-acetamide | 465.53 | 254.0-255.7 | 2.44 |
| I-55 | N-(2-Chloro-4-sulfamoyl-phenyl)-2-[4-(4-cyano-2-methyl-phenoxy)-3-methoxy-phenyl]-acetamide | 485.95 | 250.1-253.8 | 0.4187 |
| I-56 | N-(2-Bromo-4-sulfamoyl-phenyl)-2-[4-(4-cyano-2-methyl-phenoxy)-3-methoxy-phenyl]-acetamide | 530.4 | 246.3-249.3 | 0.2816 |
| I-57 | 2-[4-(3-Chloro-5-cyano-phenoxy)-3-methoxy-phenyl]-N-(4-sulfamoyl-phenyl)-acetamide | 471.92 | 198.6-199.8 | 10 |
| I-58 | 2-[4-(3-Chloro-5-cyano-phenoxy)-3-methoxy-phenyl]-N-(4-sulfamoylmethyl-phenyl)-acetamide | 485.95 | 171.3-172.7 | 10 |
| I-59 | 2-[3-Bromo-4-(4-cyano-2-methyl-phenoxy)-phenyl]-N-(2-methyl-4-sulfamoyl-phenyl)-acetamide | 514.4 | 202.1-203.1 | 0.7424 |
| I-60 | 2-[3-Bromo-4-(4-cyano-2-methyl-phenoxy)-phenyl]-N-(2-chloro-4-sulfamoyl-phenyl)-acetamide | 534.82 | 204.7-205.9 | 0.0945 |
| I-61 | 2-[3-Bromo-4-(4-cyano-2-methyl-phenoxy)-phenyl]-N-(2-bromo-4-sulfamoyl-phenyl)-acetamide | 579.27 | 204.6-205.1 | 0.0809 |
| I-62 | 2-[3-Bromo-4-(3-cyano-5-difluoromethyl-phenoxy)-phenyl]-N-(2-methyl-4-sulfamoyl-phenyl)-acetamide | 550.38 | 194.1-194.9 | 0.1163 |
| I-63 | 2-[3-Bromo-4-(3-cyano-5-difluoromethyl-phenoxy)-phenyl]-N-(2-chloro-4-sulfamoyl-phenyl)-acetamide | 570.8 | 204.9-205.5 | 0.0531 |
| I-64 | 2-[3-Bromo-4-(3-cyano-5-difluoromethyl-phenoxy)-phenyl]-N-(2-bromo-4-sulfamoyl-phenyl)-acetamide | 615.25 | 197.2-201.3 | 0.0612 |
| I-65 | 2-[4-(3-Chloro-5-cyano-phenoxy)-2,3-dimethyl-phenyl]-N-(4-sulfamoyl-phenyl)-acetamide | 469.95 | 250.3-252.1 | 3.12 |
| I-66 | 2-[4-(3-Chloro-5-cyano-phenoxy)-2,3-dimethyl-phenyl]-N-(2-methyl-4-sulfamoyl-phenyl)-acetamide | 483.97 | 225.5-228.1 | 0.0817 |

Compounds of the present invention can be prepared by well established procedures. (3-Fluoro-4-hydroxy-phenyl)-acetic acid, (4-hydroxy-3-methyl-phenyl)acetic acid, (3-bromo-4-hydroxy-phenyl)acetic acid, (4-hydroxy-3-methoxy-phenyl)acetic acid and 4-hydroxy-2,3-dimethyl-phenyl)acetonitrile are commercially available or the corresponding methyl ether and/or alkyl ester of the hydroxy acids are commercially available. Ethyl (3-chloro-4-hydroxy-phenyl)acetate was prepared from 3-chloro-4-methoxy-toluene as described in example 7. A methyl ether is readily demethylated under well known conditions with BBr$_3$, HBr or HI or LiI/collidine. A carboxylic acid can be converted to the corresponding ester by standard methodology. The fluorinated phenyl derivatives required for coupling with the phenol including 3-chloro-5-fluoro-benzonitrile, 5-fluoro-isophthalonitrile, 1-bromo-2-fluoro-4-chloro-benzene, 4-chloro-2-fluoro-benzonitrile, 1,3-dichloro-2-fluorobenzonitrile, 4-fluoro-3-methyl-benzonitrile are commercially available compounds. 3-Difluoromethyl-5-fluoro-benzonitrile was prepared from 3,5-dibromo-fluoro-benzene as described in example 11.

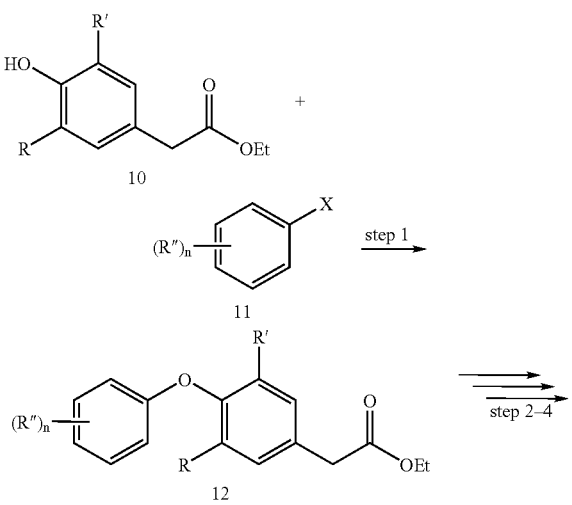

SCHEME 1

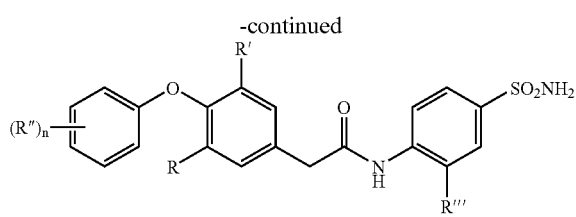

X = F, B(OH)₂ or another leaving group
R = halogen alkyl, alkoxy
R' = hydrogen or fluorine
R" = halogen, cyano, haloalkyl, alkyl, cycloalkyl
R''' = hydrogen, halogen or alkyl The general route is depicted in SCHEME 1. Both the phenoxy substituent and the phenyl ring with a pendant acetic acid are optionally substituted as described in the claims and the symbols R, R', R" and R''' are intended to generalize the SCHEME to the extent that these positions are defined in the claims and specification.

The preparation of diaryl ethers (step I supra) has been reviewed (J. S. Sawyer, *Recent Advances in Diaryl Ether Synthesis, Tetrahedron* 2000 56:5045-5065). Introduction of the aryl ether can often be accomplished by direct SNAr displacement reaction with a phenol 10 on a aromatic ring substituted with a leaving group and electronegative substituents 11 (X=leaving group). Fluoroaromatic compounds with electronegative substituents are known to be sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides undergo facile displacement reactions even at room temperature (D. Boger et al., *Biorg. Med. Chem. Lett.* 2000 10: 1471-75; F. Terrier *Nucleophilic Aromatic Displacement: The Influence of the Nitro Group* VCH Publishers, New York, N.Y. 1991). Phenols typified by 10 in SCHEME I can be treated with appropriately substituted aryl fluorine compounds to produce diaryl ethers (infra).

Aryl ethers also can be efficiently prepared by Cu(OAc)₂ catalyzed condensation of substituted benzene boronic acids (11, X=B(OH)₂) and phenols (D. A. Evans et al., *Tetrahedron Lett.*, 1998 39:2937-2940 and D. M. T. Chan et al., *Tetrahedron Lett.* 1998 39:2933-2936). This protocol can also be adapted to phenols such as 10. Benzene boronic acids with a variety of other substituents are commercially available.

Alternatively, variations of the Ullmann diaryl ether synthesis with Cu(I) salts (J.-F. Marcoux et al., *J. Am. Chem. Soc.* 1997 119:10539-540; E. Buck et al, *Org. Lett.* 2002 4(9):1623-1626) or palladium-catalyzed coupling procedures also has been reported (G. Mann et al., *J. Am. Chem. Soc.*, 1999 121:3224-3225) have been described. One skilled in the art will appreciate that optimal procedure will vary depending on the nature and position of substituents on the aryl rings to be coupled and useful conditions for the coupling can by identified without undue experimentation.

The conversion of the carboxylic ester 12 into the corresponding anilide 13 is effected by standard methodology. The carboxylic acid ester is hydrolyzed under mild base conditions to afford the corresponding carboxylic acid which is converted to the corresponding acid chloride and finally condensed with a substituted aniline.

Substituted anilines are readily available. 4-Amino-benzenesulfonamide (20) and 4-amino-3-methyl-benzenesulfonamide (21) are commercially available. Electrophilic substitution at the 3- and/or 5-position of 20 is readily achieved due to activation of the ortho positions by the amine. Thus contacting 20 with NBS or NCS affords 4-amino-3-bromo- and 4-amino-3-chloro-benzenesulfonamide respectively.

Dosage and Administration

The compounds of the present invention may be formulated in a wide variety of oral administration dosage forms and carriers. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pennsylvania. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient. In general a therapeutically effective amount of a compound of the present invention, and optionally one or more additional antiviral agents, is an amount effective to reduce the viral load or achieve a sustained viral response to therapy.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

These examples and preparations which follow are provided to enable those skilled in the art to more clearly understand and to practice the present invention. They should not be considered as limiting the scope of the invention, but merely as being illustrative and representative thereof.

EXAMPLE 1

[3-Bromo-4-(3-chloro-5-cyano-phenoxy)-phenyl]-acetic acid ethyl ester (I-46)

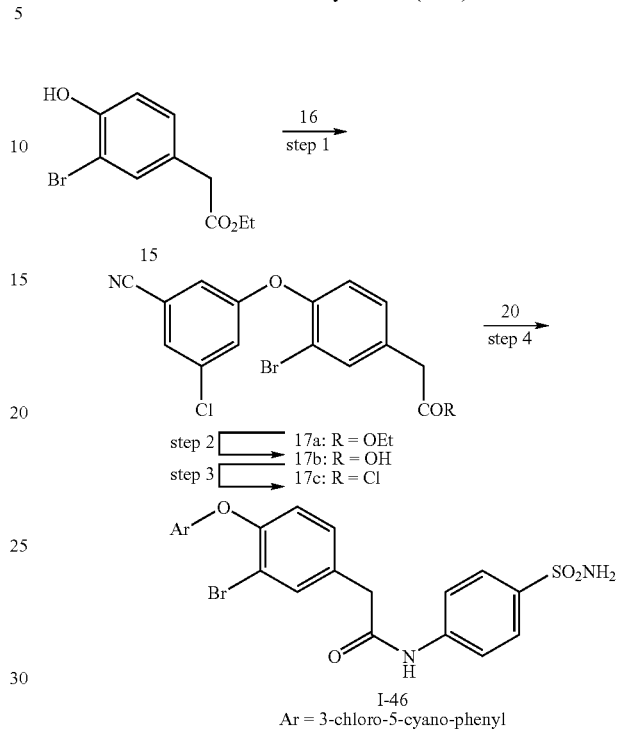

step 1—To a solution of 15 (1.6 g, 6.20 mmol) in NMP (12 mL) was added $K_2CO_3$ (2.56 g, 18.6 mmol) and 3-chloro-5-fluorobenzonitrile (16, 0.96 g, 6.20 mmol). The reaction was heated in a laboratory microwave at 110° C. for 5 min and at 120° C. for 80 min. The reaction mixture was cooled to RT and diluted with 10% aqueous HCl. The mixture was extracted 3 times with EtOAc. The combined organics were washed with $H_2O$ and brine, dried ($Na_2SO_4$), filtered and evaporated in vacuo. The crude product was purified via $SiO_2$ chromatography eluting with MeOH/hexane to afford 17a.

step 2—A solution of 17a (0.62 g, 1.57 mmol), LiOH (113 mg, 4.7 mmol) and THF/$H_2O$ (4/1, 25 mL) was stirred at RT for 1 h. The reaction was quenched by addition of 10% aqueous HCl. The mixture was extracted 3 times with DCM, the combined organics were washed with $H_2O$ and brine, dried ($Na_2SO_4$), filtered and evaporated to afford 17b which was used in the next step without further purification.

step 3—To a stirred solution of 17b (557 mg, 1.52 mmol) and DCM (7 mL) maintained under a $N_2$ atmosphere at RT was added dropwise oxalyl chloride (265 µL; 3.04 mmol) followed by 2 drops of DMF. The reaction was stirred for 1 h at RT. Excess solvent and oxalyl chloride were removed in vacuo to afford 17c which was used in the next step without any further purification.

step 4—To a stirred solution of 17c (0.22 mmol) in acetone (1 mL) under a $N_2$ atmosphere was added sequentially $NaHCO_3$ (36.5 mg, 0.434 mmol), 4-amino-benzenesulfonamide (36.4 mg, 0.22 mmol) and water (2 mL). The mixture was sonicated for 5 min and stirred overnight at RT. The reaction mixture was filtered and the solid was washed with water and $Et_2O$ and dried in vacuo to afford I-46: mp=205.3-207.4° C.; ms [M-H]=518.

EXAMPLE 2

2-[3-Chloro-4-(3,5-dicyano-phenoxy)-phenyl]-N-(4-sulfamoyl-phenyl)-acetamide (I-21)

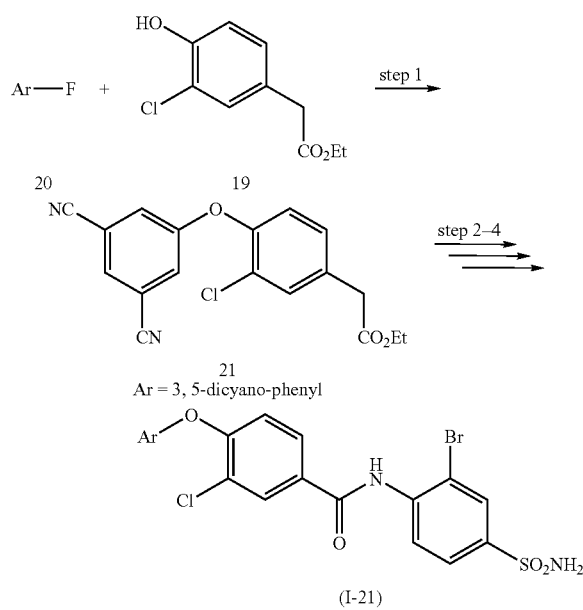

step 1—To a solution of (3-chloro-4-hydroxy-phenyl)-acetic acid ethyl ester (19, 1.34 g, 6.22 mmol) in NMP (10 mL) was added $K_2CO_3$ (2.58 g, 18.7 mmol) and 5-fluoro-isophtalonitrile (20, 1.0 g, 6.84 mmol). The reaction was heated to 100° C. for 4 h. The reaction mixture was cooled to RT, water was added, and the mixture was extracted 3 times with EtOAc. The combined extracts were washed with $H_2O$ and brine, dried ($Na_2SO_4$), filtered and evaporated in vacuo to afford 21 which was used without further purification.

Steps 2-4 were carried out as described in examples 2-4 of Example 1, except in step 4, 3-bromo-4-amino-benzenesulfonamide was used in place of 4-amino-benzenesulfonamide to afford I-21.

4-Amino-3-bromo-benzenesulfonamide—To a stirred solution of 4-amino-benzenesulfonamide (10 g, 58.1 mmol) in DMF (10 mL) cooled to 0° C. was added NBS (10.3 g, 58.1). The resulting mixture was stirred for 10 min at 0° C. then quenched by addition of water. The precipitate formed was filtered, washed with water and dried in vacuo to afford 4-amino-3-bromo-benzenesulfonamide.

2-[3-Chloro-4-(3,5-dicyano-phenoxy)-phenyl]-N-(2-trifluoromethyl-phenyl)-acetamide (I-9) was prepared analogously except in step 4, 2-trifluoromethyl-aniline was used in place of 3-bromo-4-amino-benzenesulfonamide.

2-[3-Chloro-4-(3,5-dicyano-phenoxy)-phenyl]-N-(4-methoxy-2-methyl-phenyl)-acetamide (I-10) was prepared analogously except in step 4, 2-methyl-4-methoxy-aniline was used in place of 3-bromo-4-amino-benzenesulfonamide.

2-[3-Chloro-4-(3,5-dicyano-phenoxy)-phenyl]-N-(4-dimethylsulfamoyl-phenyl)-acetamide (I-11) was prepared analogously except in step 4, 4-amino-N,N-dimethyl-benzenesulfonamide was used in place of 3-bromo-4-amino-benzenesulfonamide.

2-[3-Chloro-4-(3,5-dicyano-phenoxy)-phenyl]-N-[4-(piperidine-1-sulfonyl)-phenyl]-acetamide (I-12) was prepared analogously except in step 4, 4-(piperidine-1-sulfonyl)-phenylamine was used in place of 3-bromo-4-amino-benzenesulfonamide.

2-[3-Chloro-4-(3,5-dicyano-phenoxy)-phenyl]-N-[4-(morpholine-4-sufonyl)-phenyl]-acetamide (I-13) was prepared analogously except in step 4, 4-(morpholine-4-sulfonyl)-phenylamine was used in place of 3-bromo-4-amino-benzenesulfonamide.

2-[3-Chloro-4-(3,5-dicyano-phenoxy)-phenyl]-N-(2,3-dimethyl-phenyl)-acetamide (I-14) was prepared analogously except in step 4, 2,3-dimethyl-phenylamine was used in place of 3-bromo-4-amino-benzenesulfonamide.

2-[3-Chloro-4-(3,5-dicyano-phenoxy)-phenyl]-N-(2-ethyl-phenyl)-acetamide (I-15) was prepared analogously except in step 4, 2-ethyl-phenylamine was used in place of 3-bromo-4-amino-benzenesulfonamide.

2-[3-Chloro-4-(3,5-dicyano-phenoxy)-phenyl]-N-o-tolyl-acetamide (I-16) was prepared analogously except in step 4, 2-methyl-phenylamine was used in place of 3-bromo-4-amino-benzenesulfonamide.

2-[3-Chloro-4-(3,5-dicyano-phenoxy)-phenyl]-N-(2-methoxy-phenyl)-acetamide (I-1 7) was prepared analogously except in step 4, 2-methoxy-phenylamine was used in place of 3-bromo-4-amino-benzenesulfonamide.

2-[3-Chloro-4-(3,5-dicyano-phenoxy)-phenyl]-N-(2-isopropyl-phenyl)-acetamide (I-19) was prepared analogously except in step 4, 2-isopropyl-phenylamine was used in place of 3-bromo-4-amino-benzenesulfonamide.

N-(2-Bromo-phenyl)-2-[3-chloro-4-(3,5-dicyano-phenoxy)-phenyl]-acetamide (I-20) was prepared analogously except in step 4, 2-bromo-phenylamine was used in place of 3-bromo-4-amino-benzenesulfonamide.

2-[3-Chloro-4-(3, 5-dicyano-phenoxy)-phenyl]-N-(4-cyano-phenyl)-acetamide (I-22) was prepared analogously except in step 4, 4-amino-benzonitrile was used in place of 3-bromo-4-amino-benzenesulfonamide.

(4-{2-[3-Chloro-4-(3,5-dicyano-phenoxy)-phenyl]-acetylamino}-phenoxy)-acetic acid methyl ester (I-26) was prepared analogously except in step 4, (4-amino-phenoxy)-acetic acid methyl ester was used in place of 3-bromo-4-amino-benzenesulfonamide.

2-[3-Chloro-4-(3,5-dicyano-phenoxy)-phenyl]-N-(4-cyanomethoxy-phenyl)-acetamide (I-27) was prepared analogously except in step 4, (4-amino-phenoxy)-acetonitrile was used in place of 3-bromo-4-amino-benzenesulfonamide.

(4-{2-[3-Chloro-4-(3,5-dicyano-phenoxy)-phenyl]-acetylamino}-phenylsulfanyl)-acetic acid methyl ester (I-28) was prepared analogously except in step 4, (4-amino-phenylsulfanyl)-acetic acid methyl ester was used in place of 3-bromo-4-amino-benzenesulfonamide.

2-[3-Chloro-4-(3,5-dicyano-phenoxy)-phenyl]-N-(2-cyano-phenyl)-acetamide (I-29) was prepared analogously except in step 4, 2-amino-benzonitrile was used in place of 3-bromo-4-amino-benzenesulfonamide.

4-{2-[3-Chloro-4-(3,5-dicyano-phenoxy)-phenyl]-acetylamino}-benzoic acid methyl ester (I-30) was prepared analogously except in step 4, 4-amino-benzoic acid methyl ester was used in place of 3-bromo-4-amino-benzenesulfonamide.

4-{2-[3-Chloro-4-(3,5-dicyano-phenoxy)-phenyl]-acetylamino}-3-methyl-benzoic acid methyl ester (I-31) was prepared analogously except in step 4, 4-amino-3-methyl-benzoic acid methyl ester was used in place of 3-bromo-4-amino-benzenesulfonamide.

3-Chloro-4-{2-[3-chloro-4-(3,5-dicyano-phenoxy)-phenyl]-acetylamino}-benzoic acid methyl ester (I-32) was prepared analogously except in step 4, 4-amino-3-chloro-benzoic acid methyl ester was used in place of 3-bromo-4-amino-benzenesulfonamide.

EXAMPLE 3

2-[4-(2-Bromo-5-chloro-phenoxy)-3-chloro-phenyl]-N-o-tolyl-acetamide (I-7)

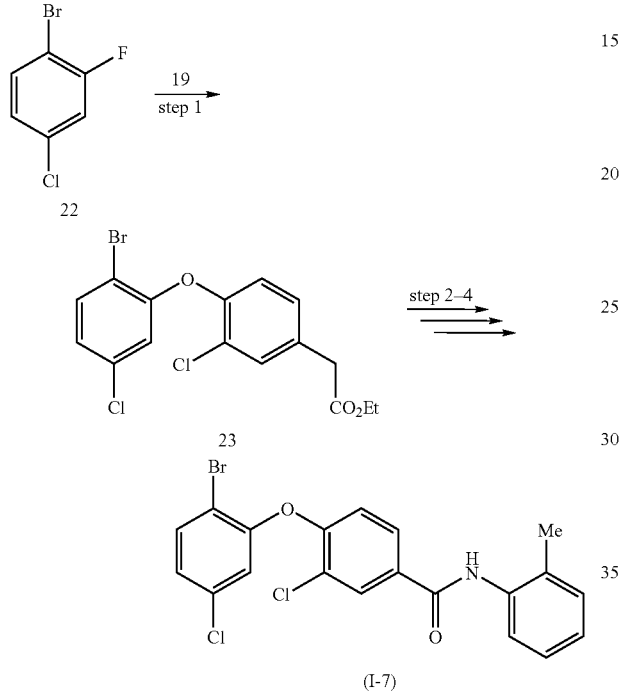

step 1—To a solution of (3-chloro-4-hydroxy-phenyl)-acetic acid ethyl ester (19, 2.0 g, 9.32 mmol) in NMP (20 mL) was added $K_2CO_3$ (3.86 g, 28.0 mmol) and 1-bromo-4-chloro-2-fluoro-benzene (20, 1.28 ml, 10.3 mmol). The reaction was heated to 100° C. for 6 h. The reaction mixture was cooled to RT, water was added and the mixture was extracted 3 times with EtOAc. The combined organics were washed with $H_2O$ and brine, dried ($Na_2SO_4$), filtered and evaporated in vacuo to afford 23 which was used without further purification.

Steps 2-4 were carried out as described in examples 2-4 of Example 1, except in step 4, 2-methyl-phenylamine was used in place of 4-amino-benzenesulfonamide to afford I-7.

2-[4-(2-Bromo-5-chloro-phenoxy)-3-chloro-phenyl]-N-(4-sulfamoyl-phenyl)-acetamide (I-3) was prepared analogously except in step 4, 4-amino-benzenesulfonamide was used in place of 3-bromo-4-amino-benzenesulfonamide.

2-[4-(2-Bromo-5-chloro-phenoxy)-3-chloro-phenyl]-N-[2-methyl-4-(3-sulfamoyl-propoxy)-phenyl]-acetamide (I-5) was prepared analogously except in step 4, 3-(4-amino-3-methyl-phenoxy)-propane-1-sulfonic acid amide was used in place of 3-bromo-4-amino-benzenesulfonamide.

2-[4-(2-Bromo-5-chloro-phenoxy)-3-chloro-phenyl]-N-(2-fluoro-phenyl)-acetamide (I-8) was prepared analogously except in step 4, 2-fluoro-phenylamine was used in place of 3-bromo-4-amino-benzenesulfonamide.

2-[4-(2-Bromo-5-chloro-phenoxy)-3-chloro-phenyl]-N-(2-chloro-phenyl)-acetamide (I-6) was prepared analogously except in step 4, 2-chloro-phenylamine was used in place of 3-bromo-4-amino-benzenesulfonamide.

EXAMPLE 4

2-[3-Chloro-4-(2-chloro-5-cyano-phenoxy)-phenyl]-N-(4-sulfamoyl-phenyl)-acetamide (I-34)

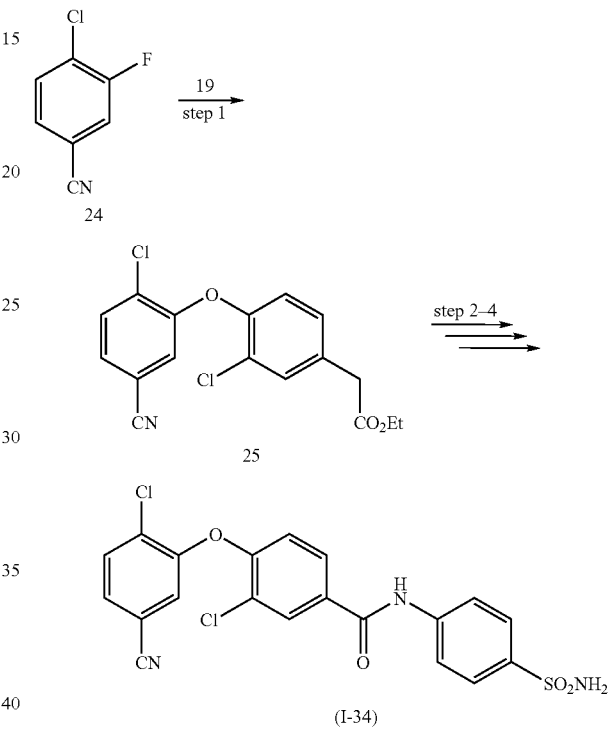

step 1—To a solution of (3-chloro-4-hydroxy-phenyl)-acetic acid ethyl ester (19, 3.0 g, 14.0 mmol) in NMP (20 mL) was added $K_2CO_3$ (5.80 g, 41.9 mmol) and 4-chloro-3-fluoro-benzonitrile (24, 2.17 g, 14.0 mmol). The reaction was heated to 120° C. overnight. The reaction mixture was cooled to RT, water was added and the mixture was extracted 3 times with EtOAc. The combined organics were washed with $H_2O$ and brine, dried ($Na_2SO_4$) filtered and evaporated in vacuo to afford 25 which was used in subsequent steps without further purification.

Steps 2-4 to convert the ester from step 1 to I-34 were run as described for steps 2-4 of example 1.

2-[3-Chloro-4-(2-chloro-5-cyano-phenoxy)-phenyl]-N-(2-methyl-4-sulfamoyl-phenyl)-acetamide (I-35) was prepared analogously except in step 4, 4-amino-3-methyl-benzenesulfonamide was used in place of 4-amino-benzenesulfonamide.

2-[3-Chloro-4-(2-chloro-5-cyano-phenoxy)-phenyl]-N-(2-chloro-4-sulfamoyl-phenyl)-acetamide (I-36) was prepared analogously except in step 4, 4-amino-3-chloro-benzenesulfonamide was used in place of 4-amino-benzenesulfonamide.

EXAMPLE 5

2-[3-Chloro-4-(2,6-dichloro-phenoxy)-phenyl]-N-(4-sulfamoyl-phenyl)-acetamide (I-40)

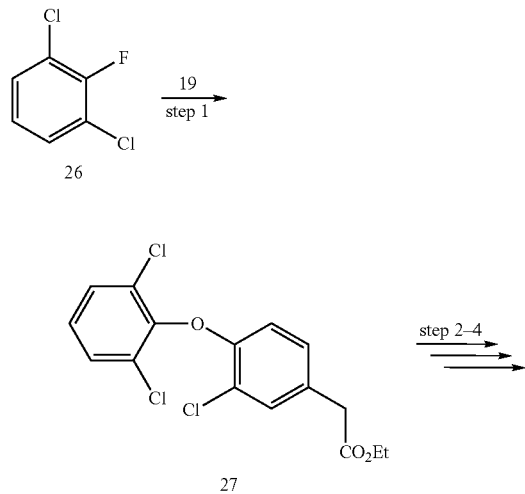

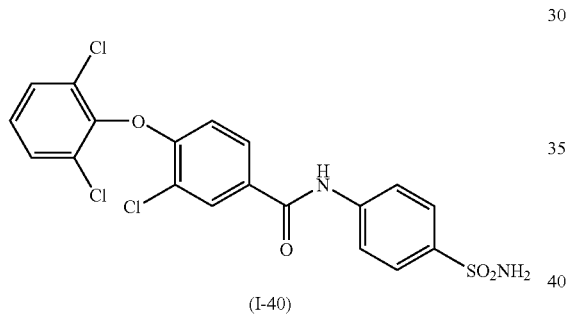

EXAMPLE 6

2-[3-Chloro-4-(4-cyano-2-methyl-phenoxy)-phenyl]-N-(4-sulfamoyl-phenyl)-acetamide (I-42)

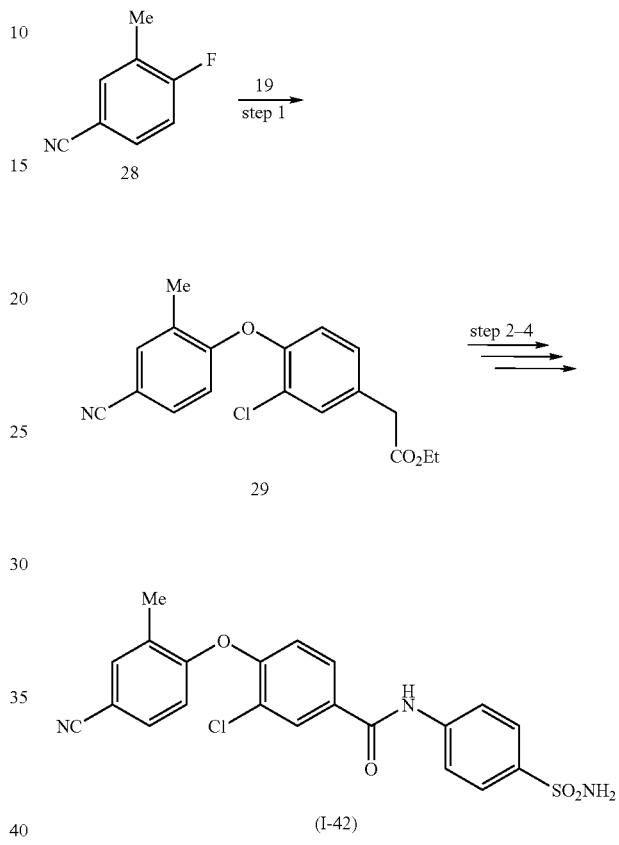

step 1—To a solution of 19 (3.0 g, 14.0 mmol) in NMP (20 mL) was added K$_2$CO$_3$ (5.80 g, 41.9 mmol) and 1,3-dichloro-2-fluoro-benzene (26, 2.31 g, 14.0 mmol). The reaction was heated to 120° C. overnight. The reaction mixture was cooled to RT, diluted with H$_2$O and extracted 3 times with EtOAc. The combined extracts were washed with H$_2$O and brine, dried (Na$_2$SO$_4$), filtered and evaporated in vacuo to afford 27 which was used in subsequent steps without further purifications.

Steps 2-4 to convert the ester 27 from step 1 to I-40 were run as described for steps 2-4 of example 1.

2-[3-Chloro-4-(2,6-dicloro-phenoxy)-phenyl]-N-(2-methyl-4-sulfamoyl-phenyl)-acetamide (I-41) was prepared analogously except in step 4, 4-amino-3-methyl-benzenesulfonamide was used in place of 4-amino-benzenesulfonamide.

2-[3-Chloro-4-(2,6-dichloro-phenoxy)-phenyl]-N-(2-chloro-4-sulfamoyl-phenyl)-acetamide (I-45) was prepared analogously except in step 4, 4-amino-3-chloro-benzenesulfonamide was used in place of 4-amino-benzenesulfonamide.

step 1—To a solution of 19 (3.0 g, 14.0 mmol) in NMP (20 mL) was added K$_2$CO$_3$ (5.80 g, 41.9 mmol) and 4-fluoro-3-methyl-benzonitrile (28, 1.89 g, 14.0 mmol). The reaction was heated to 120° C. overnight. The reaction mixture was cooled to RT, diluted with H$_2$O and extracted 3 times with EtOAc. The combined extracts were washed with H$_2$O and brine, dried (Na$_2$SO$_4$), filtered and evaporated in vacuo to afford 29 which was used in subsequent steps without further purification.

Steps 2-4 to convert the ester 29 from step 1 to I-42 were run as described for steps 2-4 of example 1.

2-[3-Chloro-4-(4-cyano-2-methyl-phenoxy)-phenyl]-N-(2-methyl-4-sulfamoyl-phenyl)-acetamide (I-43) was prepared analogously except in step 4, 4-amino-3-methyl-benzenesulfonamide was used in place of 4-aminobenzenesulfonamide.

2-[3-Chloro-4-(4-cyano-2-methyl-phenoxy)-phenyl]-N-(2-chloro-4-sulfamoyl-phenyl)-acetamide (I-44) was prepared analogously except in step 4, 4-amino-3-chloro-benzenesulfonamide was used in place of 4-aminobenzenesulfonamide.

EXAMPLE 7

2-[3-Chloro-4-(3-chloro-5-cyano-phenoxy)-phenyl]-N-(4-sulfamoyl-phenyl)-acetamide (I-37)

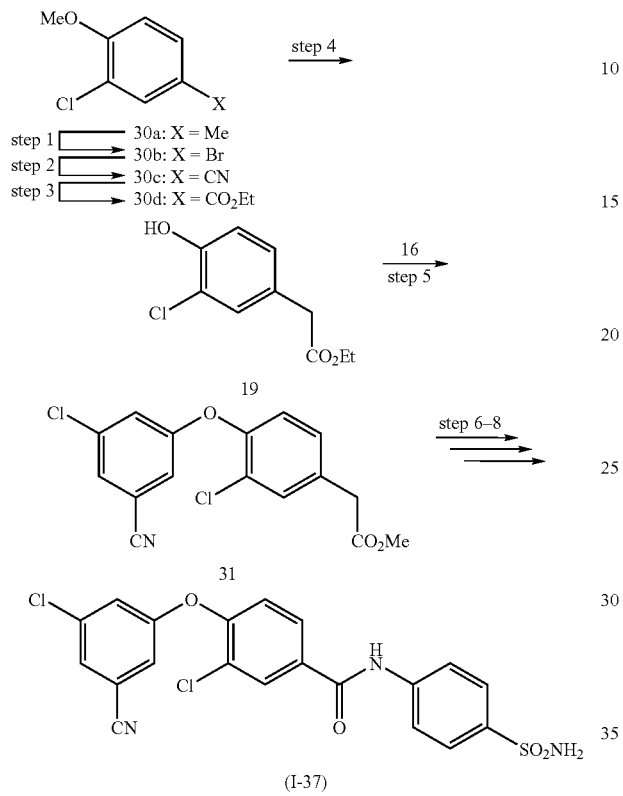

step 1—A solution of 4-chloro-3-methoxy-toluene (30a; 0.5 g; 3.2 mmol), NBS (0.57 g; 3.2 mmol) and benzoyl peroxide (0.031 g; 0.13 mmol) and 32 mL of DCE were heated at reflux for 3 h. The reaction mixture was cooled, diluted with DCM and washed with water and brine. The organic extract was dried, filtered and evaporated to yield the bromomethyl compound 30b which was used without further purification.

step 2—The 28 g (0.166 mmol) of 30b from the previous step, NaCN (28 g; 0.58 mmol; 3.5 equiv.) and 500 mL of 90% aqueous EtOH were stirred at RT overnight. The crude residue was partitioned between EtOAc/H$_2$O (359 mL of each), washed with brine, dried, filtered and evaporated. The crude product was purified by SiO$_2$ chromatography eluting with a EtOAc/hexane gradient (100 to 90% hexane) to afford 21 g of 30c.

step 3—Gaseous HCl was slowly bubbled into a cooled solution of 4-chloro-3-methoxyacetonitrile (30c) in toluene (10 mL), ether (10 mL) and EtOH (1 mL) for about 10 min. The reaction was stoppered and stored at −30° C. for one week. TLC failed to detect any remaining starting material. The solvent was evaporated and the yellow solid was stirred with Et$_2$O, filtered and washed with Et$_2$O and dried in a vacuum oven to yield 0.57 g (90%) of ethyl 4-chloro-3-methoxyphenylmethylimidate (30, X=C(=NH)OEt)). A solution of the imidate (0.57 g) and H$_2$O (10 mL) was heated at 40° C. for 3 h. The reaction was cooled to RT and extracted with EtOAc. The reaction was dried (MgSO$_4$), filtered and evaporated and the resulting product 30d was used without further purification.

step 4—A solution of ethyl 4-chloro-3-methoxyphenylacetate (30d; 36 g; 157 mmol) and DCM (2 L) was cooled to −78° C. and a solution of BBr$_3$ (74 mL; 785 mmol; 1.0 M in DCM) was added over 30 min. After 1 h at −78° C. the reaction was allowed to warm to RT. When starting material was consumed the reaction was cooled in an ice-water bath and the reaction quenched with 200 mL of water. The aqueous phase was extracted with DCM:EtOAc (4:1 v/v). The combined extracts were washed with water and brine, dried (Na$_2$SO$_4$), filtered and evaporated to afford 30 g (90%) of 19.

step 5—A solution of 19 (1.07 g, 5 mmol), 16 (1.3 g, 7.56 mmol), K$_2$CO$_3$ (2.07 g, 15.0 mmol) and NMP (10 mL) was stirred and heated to 110° C. for 6 h. The reaction mixture was cooled to RT and diluted with H$_2$O (50 mL) and twice extracted with EtOAc. The combined organic extracts were washed sequentially with water and brine, dried (Na$_2$SO$_4$), filtered and concentrated in vacuo. The crude product was purified by SiO$_2$ chromatography eluting with EtOAc/hexane (10:90) to afford 0.328 g of 31.

Steps 6-8 to convert the ester 31 from step 5 to I-37 were run as described for steps 2-4 of example 1.

2-[3-Chloro-4-(3-chloro-5-cyano-phenoxy)-phenyl]-N-(2-methyl-4-sulfamoyl-phenyl)-acetamide (I-38) was prepared analogously except in step 8, 4-amino-3-methyl-benzenesulfonamide was used in place of 4-amino-benzenesulfonamide.

2-[3-Chloro-4-(3-chloro-5-cyano-phenoxy)-phenyl]-N-(2-chloro-4-sulfamoyl-phenyl)-acetamide (I-39) was prepared analogously except in step 8, 4-amino-3-chloro-benzenesulfonamide was used in place of 4-amino-benzenesulfonamide.

EXAMPLE 8

2-[3-Bromo-4-(3-chloro-5-cyano-phenoxy)-phenyl]-N-(4-sulfamoyl-phenyl)-acetamide (I-46)

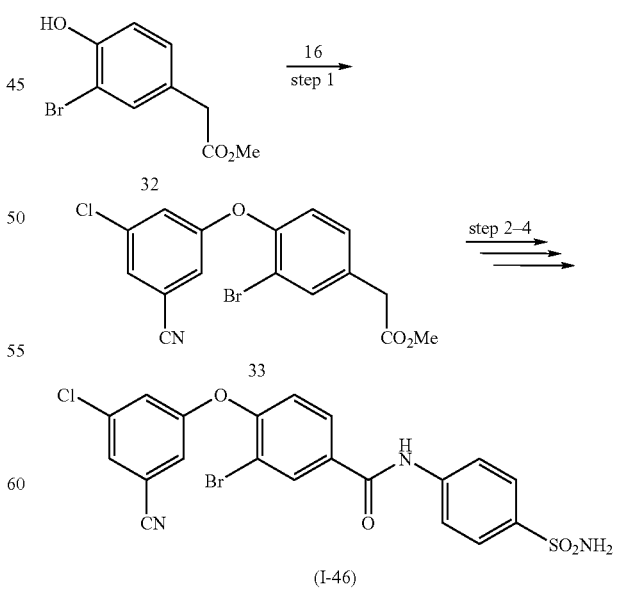

step 1—To a solution of (3-bromo-4-hydroxy-phenyl)-acetic acid ethyl ester (32, 1.6 g, 6.20 mmol) in NMP (12 mL) was added K$_2$CO$_3$ (2.56 g, 18.6 mmol) and 16 (0.96 g, 6.20 mmol). The reaction was heated in a laboratory microwave at 110° C. for 5 min and at 120° C. for 80 min. The reaction mixture was cooled to RT and HCl (10%) was added. The mixture was thrice extracted with EtOAc. The combined extracts were washed with H$_2$O and brine, dried (Na$_2$SO$_4$), filtered and evaporated in vacuo. The crude product was purified via SiO$_2$ chromatography eluting with hexane/EtOAc to afford 33.

Steps 2-4 were carried out as described for steps 2-4 of example 1 which afforded I-46: mp=205.3-207.4° C., ms, [M-H]=518.

2-[3-Bromo-4-(3-chloro-5-cyano-phenoxy)-phenyl]-N-(2-methyl-4-sulfamoyl-phenyl)-acetamide (I-47) was prepared analogously except in step 4, 4-amino-3-methyl-benzenesulfonamide was used in place of 4-amino-benzenesulfonamide: mp=214.6-215.9° C.; ms [M-H]=532.

2-[3-Bromo-4-(3-chloro-5-cyano-phenoxy)-phenyl]-N-(2-chloro-4-sulfamoyl-phenyl)-acetamide (I-48) was prepared analogously except in step 4, 4-amino-3-chloro-benzenesulfonamide was used in place of 4-amino-benzenesulfonamide: mp=205.0-207.3° C.; ms [M-H]=552.

2-[3-Bromo-4-(3-chloro-5-cyano-phenoxy)-phenyl]-N-(4-sulfamoylmethyl-phenyl)-acetamide (I-49) was prepared analogously except in step 4, (4-amino-phenyl)-methanesulfonamide was used in place of 4-amino-benzenesulfonamide: mp=133.4-135.3° C.; ms [M-H]=532.

(4-Amino-phenyl)-methanesulfonamide was prepared by the following procedure:

step 1—To a stirred solution of conc. NH$_4$OH (17 mL) in THF (34 mL) cooled to 0° C. was added dropwise (4-nitrophenyl)-methanesulfonyl chloride (2 g, 8.42 mmol). The reaction was stirred at 0° C. for 15 min then poured into ice-water and extracted 3 times with EtOAc. The combined organics were washed with water and brine, dried (Na$_2$SO$_4$), filtered and evaporated in vacuo to afford sulfonamide (4-nitro-phenyl)methanesulfonamide.

step 2—To a solution of (4-nitro-phenyl)-methanesulfonamide (1.18 g, 5.41 mmol) in EtOH (120 mL) was added Pd/C (10%, 118 mg). The mixture was stirred overnight under H$_2$ (balloon pressure), the catalyst was filtered off on a CELITE® pad and the filter cake was washed with EtOH. The filtrate was concentrated in vacuo to afford (4-amino-phenyl)-methanesulfonamide.

2-[3-Bromo-4-(3-chloro-5-cyano-phenoxy)-phenyl]-N-(2-bromo-4-sulfamoyl-phenyl)-acetamide (I-50) was prepared analogously except in step 4, 4-amino-3-bromo-benzenesulfonamide was used in place of 4-amino-benzenesulfonamide: mp=168.1-170.4° C.; ms [M-H]=596.

EXAMPLE 9

2-[4-(3-Chloro-5-cyano-phenoxy)-3-methoxy-phenyl]-N-(2-methyl-4-sulfamoyl-phenyl)-acetamide (I-51)

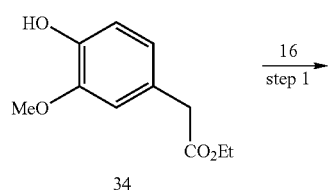

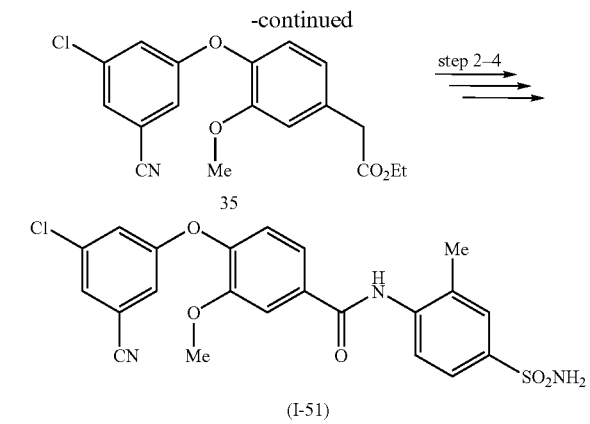

step 1—To a solution of (4-hydroxy-3-methoxy-phenyl)-acetic acid ethyl ester (34, 2.0 g, 9.51 mmol) in NMP (10 mL) was added K$_2$CO$_3$ (3.94 g, 28.5 mmol) and 16 (1.48 g, 9.51 mmol). The reaction was heated at 100° C. for 5 h. The reaction mixture was cooled to RT and HCl (10%) was added. The mixture was extracted 3 times with EtOAc. The combined organics were washed with H$_2$O and brine, dried over Na$_2$SO$_4$, filtered and evaporated in vacuo. The crude product was purified by SiO$_2$ chromatography eluting with hexane/EtOAc to afford 35.

Steps 2-4 were run as described for steps 2-4 of example 1, except in step 4, 4-amino-3-methyl-benzenesulfonamide was used in place of 4-amino-benzenesulfonamide which afforded I-51.

2-[4-(3-Chloro-5-cyano-phenoxy)-3-methoxy-phenyl]-N-(2-chloro4-sulfamoyl-phenyl)-acetamide (I-52) was prepared analogously except in step 4, 4-amino-3-chloro-benzenesulfonamide was used in place of 4-amino-3-methyl-benzenesulfonamide.

N-(2-Bromo-4-sulfamoyl-phenyl)-2-[4-(3-chloro-5-cyano-phenoxy)-3-methoxy-phenyl]-acetamide (I-53) was prepared analogously except in step 4, 4-amino-3-bromo-benzenesulfonamide was used in place of 4-amino-3-methyl-benzenesulfonamide.

2-[4-(3-Chloro-5-cyano-phenoxy)-3-methoxy-phenyl]-N-(4-sulfamoyl-phenyl)-acetamide (I-57) was prepared analogously except in step 4, 4-amino-benzenesulfonamide was used in place of 4-amino-3-methyl-benzenesulfonamide.

2-[4-(3-Chloro-5-cyano-phenoxy)-3-methoxy-phenyl]-N-(4-sulfamoylmethyl-phenyl)-acetamide (I-58) was prepared analogously except in step 4, (4-amino-phenyl)-methanesulfonamide was used in place of 4-amino-3-methyl-benzenesulfonamide

EXAMPLE 10

2-[4-(4-Cyano-2-methyl-phenoxy)-3-methoxy-phenyl]-N-(2-methyl-4-sulfamoyl-phenyl)-acetamide (I-54)

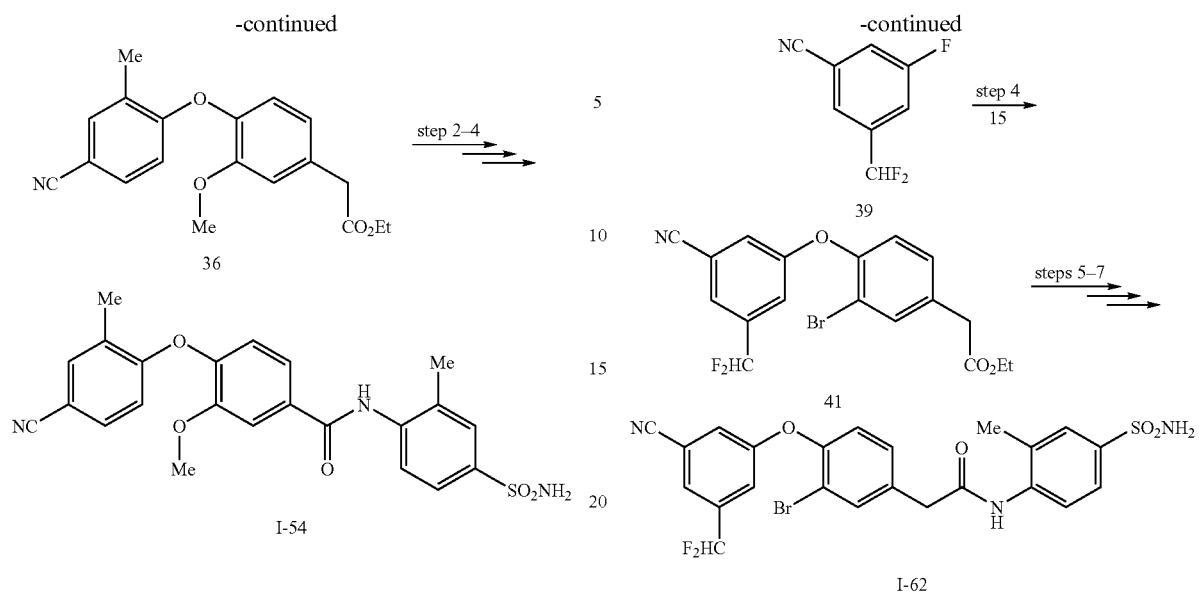

2-[4-(4-Cyano-2-methyl-phenoxy)-3-methoxy-phenyl]-N-(2-methyl-4-sulfamoyl-phenyl)-acetamide (I-54) was prepared by the procedure described in Example 1 except in step 1, 4-fluoro-3-methyl benzonitrile (28) was used in place of 3-chloro-5-fluoro-benzonitrile and in step 4, 4-amino-3-methyl-benzenesulfonamide was used in place of 4-amino-benzenesulfonamide.

N-(2-Chloro-4-sulfamoyl-phenyl)-2-[4-(4-cyano-2-methyl-phenoxy)-3-methoxy-phenyl]-acetamide (I-55) was prepared by the procedure described in Example 1 except in step 1, 4-fluoro-3-methyl benzonitrile was used in place of 3-chloro-5-fluoro-benzonitrile and in step 4, 4-amino-3-chloro-benzenesulfonamide was used in place of 4-amino-benzenesulfonamide.

N-(2-Bromo-4-sulfamoyl-phenyl)-2-[4-(4-cyano-2-methyl-phenoxy)-3-methoxy-phenyl]-acetamide (I-56) was prepared by the procedure described in Example 1 except in step 1, 4-fluoro-3-methyl benzonitrile was used in place of 3-chloro-5-fluoro-benzonitrile and in step 4, 4-amino-3-bromo-benzenesulfonamide was used in place of 4-amino-benzenesulfonamide.

EXAMPLE 11

2-[3-Bromo-4-(3-cyano-5-difluoromethyl-phenoxy)-phenyl]-N-(2-methyl-4-sulfamoyl-phenyl)-acetamide (I-62)

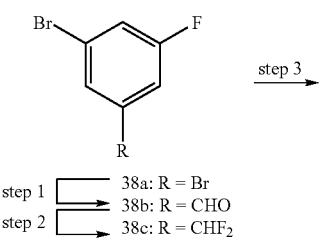

step 1—To a solution of 38a (25.39 g, 0.1 mol) and anhydrous $Et_2O$ (125 mL) cooled to −78° C. and maintained under an Ar atmosphere was added dropwise over 30 min n-BuLi (40 mL, 0.1 mol, 2.5M in hexane). The yellow solution was stirred at −78° C. for 10 min. To the reaction mixture was added dropwise dry DMF (8.52 mL, 2.2 mmol) over 5 min and the reaction stirred at −78° C. for 10 min before the cooling bath was removed and the reaction allowed to warm to −30° C. over 30 min. The reaction vessel was placed in an ice-water bath and warmed to −10° C. The mixture was slowly added to an ice cold saturated aqueous $NH_4Cl$ solution (400 mL). The organic layer was separated and the aqueous phase thrice extracted with $Et_2O$. The combined extracts were washed with water, dried ($MgSO_4$), filtered and evaporated to afford an oil which solidified on standing. The crude product was purified by $SiO_2$ chromatography eluting with a hexane/EtOAc gradient (3 to 5% EtOAc) to afford 15 g of 38b.

step 2—To a solution of 38b (32.4 g, 0.15 mol) and DCM (160 mL) cooled to −10° C. in an ice/MeOH/water bath under an Ar atmosphere in a septum-capped 1 L Nalgene narrow-neck bottle is added dropwise DAST (35.85 mL. 0.27 mol). The reaction mixture was stirred overnight. The reaction mixture was added dropwise over a 30 min period to saturated aqueous $NaHCO_3$ (400 mL) cooled to 0° C. Additional saturated $NaHCO_3$ was added to maintain the reaction at a slightly basic pH. The phases were separated and the aqueous phase was extracted twice with $Et_2O$ and the combined extracts dried ($MgSO_4$) and concentrated at 30° C. under house vacuum to afford 36 g of an orange oil which was purified by bulb-to-bulb distillation in a Kugel-Rohr at 100° C. under house vacuum to afford 30.65 g of 38c.

step 3—A solution of 38c (41.6 g, 0.182 mol), Pd[P(Ph)$_3$]$_4$(0) (15 g, 13 mmol), and zinc cyanide (12.82 g, 0.109 mol) in dry DMF (400 mL) under nitrogen was heated to 80° C. for 5.5 h. The reaction mixture was cooled to RT, the yellow solid filtered and the filtrate added to water (500 mL). The filtrate was thrice extracted with $Et_2O$ and the combined extracts washed twice with water, dried ($MgSO_4$), filtered and evaporated at 30° C. The crude was purified by $SiO_2$ chromatography eluting with a hexane/EtOAc gradient (100:0 to 95:5 to 90:10) to provide 26.3 g of 39 as a colorless oil which partially crystallizes.

step 4—To a solution of 15 (0.500 g; 1.920 mmol) and NMP (4 mL) was added $K_2CO_3$ (0.796 g; 5.76) and 3-fluoro-5-(difluoromethyl)-benzonitrile (39, 0.362 g; 2.11 mmol). The reaction was heated to 120° C. and monitored by TLC. After 8 h the reaction was cooled to RT and 10% HCl was added. The mixture was extracted with EtOAc and the combined extracts were washed with $H_2O$ and brine. The extracts were dried ($Na_2SO_4$) filtered and evaporated. The crude product was purified by $SiO_2$ chromatographed eluting with a gradient of hexane/EtOAc (0 to 40% EtOAc) to afford 41.

Steps 5-7 were run as described for steps 2-4 of example 1, except in step 4, 4-amino-3-methyl-benzenesulfonamide was used in place of 4-amino-benzenesulfonamide which afforded I-62.

2-[3-Bromo-4-(3-cyano-5-difluoromethyl-phenoxy)-phenyl]-N-(2-chloro-4-sulfamoyl-phenyl)-acetamide (I-63) was prepared analogously except in step 4, 4-amino-3-chloro-benzenesulfonamide was used in place of 4-amino-3-methyl-benzenesulfonamide.

2-[3-Bromo-4-(3-cyano-5-difluoromethyl-phenoxy)-phenyl]-N-(2-bromo-4-sulfamoyl-phenyl)-acetamide I-64) was prepared analogously except in step 4, 4-amino-3-bromo-benzenesulfonamide was used in place of 4-amino-3-methyl-benzenesulfonamide.

EXAMPLE 12

2-[3-Bromo-4-(4-cyano-2-methyl-phenoxy)-phenyl]-N-(2-methyl-4-sulfamoyl-phenyl)-acetamide (I-59)

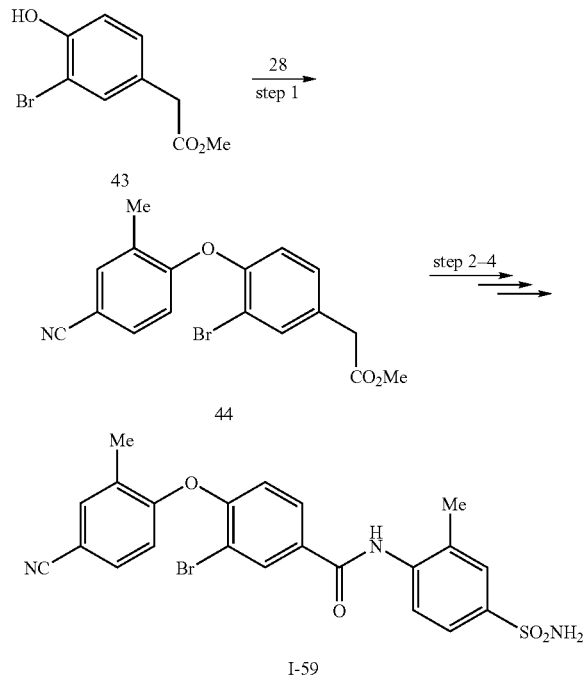

2-[3-Bromo-4-(4-cyano-2-methyl-phenoxy)-phenyl]-N-(2-methyl-4-sulfamoyl-phenyl)-acetamide (I-59) was prepared by the procedure described in Example 1 except in step 1, 4-fluoro-2-methyl benzonitrile was used in place of 3-chloro-5-fluoro-benzonitrile and in step 4, 4-amino-3-methyl-benzenesulfonamide was used in place of 4-amino-benzenesulfonamide.

2-[3-Bromo-4-(4-cyano-2-methyl-phenoxy)-phenyl]-N-(2-chloro-4-sulfamoyl-phenyl)-acetamide (I-60) was prepared by the procedure described in Example 1 except in step 1, 4-fluoro-2-methyl benzonitrile was used in place of 3-chloro-5-fluoro-benzonitrile and in step 4, 4-amino-3-chloro-benzenesulfonamide was used in place of 4-amino-benzenesulfonamide.

2-[3-Bromo-4-(4-cyano-2-methyl-phenoxy)-phenyl]-N-(2-bromo-4-sulfamoyl-phenyl)-acetamide (I-61) was prepared by the procedure described in Example 1 except in step 1, 4-fluoro-2-methyl benzonitrile was used in place of 3-chloro-5-fluoro-benzonitrile and in step 4, 4-amino-3-bromo-benzenesulfonamide was used in place of 4-amino-benzenesulfonamide.

EXAMPLE 13

2-[4-(3-Chloro-5-cyano-phenoxy)-2,3-dimethyl-phenyl]-N-(4-sulfamoyl-phenyl)-acetamide (I-65)

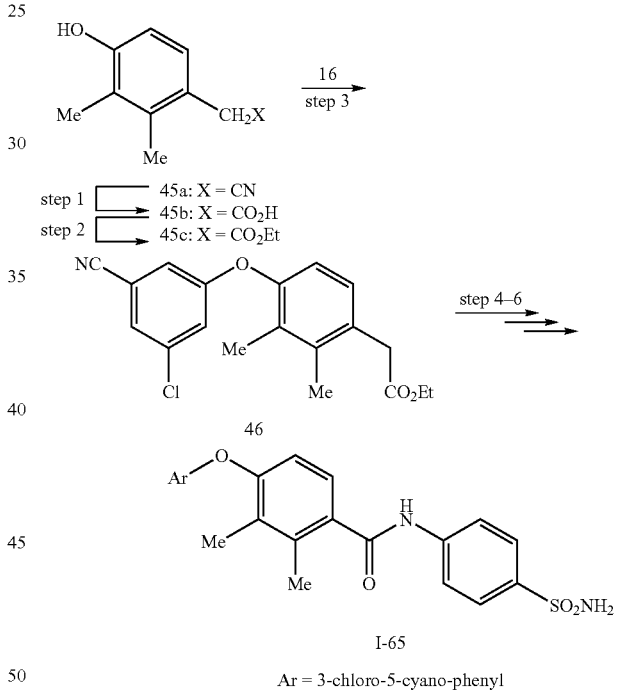

Ar = 3-chloro-5-cyano-phenyl (4-Hydroxy-2,3-dimethyl-phenyl)-acetic acid ethyl ester step 1—A mixture of (4-hydroxy-2,3-dimethyl-phenyl)-acetonitrile (45a, 6 g), glacial HOAc (60 mL) and HBr (48%, 60 mL) was stirred at 110° C. for 3 h. The reaction was cooled at RT and EtOAc was added, the organic phase was separated and washed twice with brine, dried ($Na_2SO_4$), filtered and evaporated in vacuo to afford 45b.

step 2—A mixture of 45b (4.82 g), $H_2SO_4$ (4.8 mL) in EtOH (100 mL) was stirred at 75° C. for 3h. The reaction was cooled at RT and the solvent was removed in vacuo. The residue was partitioned between EtOAc and brine, the organic phase was separated and washed with brine, dried ($Na_2SO_4$), filtered and evaporated in vacuo to afford 45c.

Steps 3-6 were carried by the procedures described in Example 1 except in step 1, [3-(3-chloro-5-cyano-phenoxy)-

4,5-dimethyl-phenyl]-acetic acid ethyl ester was used in place of [3-bromo-4-(3-chloro-5-cyano-phenoxy)-phenyl]-acetic acid ethyl.

2-[4-(3-Chloro-5-cyano-phenoxy)-2,3-dimethyl-phenyl]-N-(2-methyl-4-sulfamoyl-phenyl)-acetamide (I-66) was prepared by the procedure described for I-65 except in step 6, 4-amino-3-methyl-benzenesulfonamide was used in place of 4-amino-benzenesulfonamide.

2-[4-(3-Chloro-5-cyano-phenoxy)-2,3-dimethyl-phenyl]-N-(2-chloro-4-sulfamoyl-phenyl)-acetamide (I-18) was prepared by the procedure described for I-65 except in step 6, 4-amino-3-chloro-benzenesulfonamide was used in place of 4-amino-benzenesulfonamide.

N-(2-Bromo-4-sulfamoyl-phenyl)-2-[4-(3-chloro-5-cyano-phenoxy)-2,3-dimethyl-phenyl]-acetamide (I-33) was prepared by the procedure described for I-65 except in step 6, 4-amino-3-bromo-benzenesulfonamide was used in place of 4-amino-benzenesulfonamide.

EXAMPLE 14

N-(2-Chloro-4-sulfamoyl-phenyl)-2-[4-(4-cyano-2-methyl-phenoxy)-2,3-dimethyl-phenyl]-acetamide (I-25)

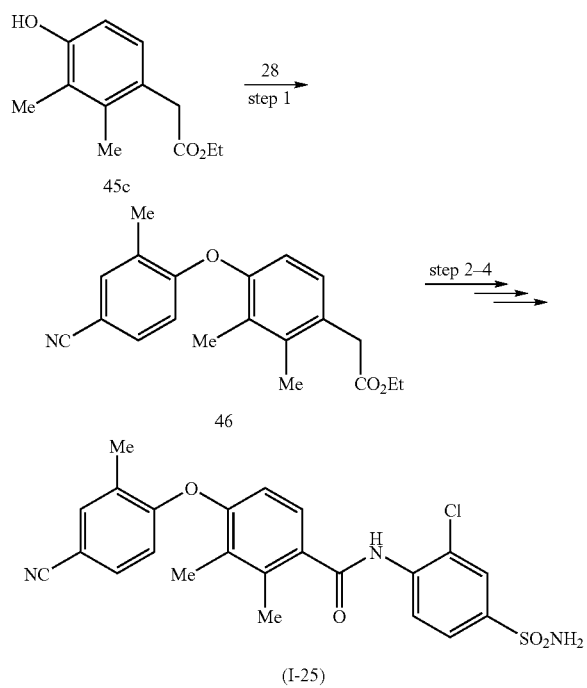

(4-Hydroxy-2,3-dimethyl-phenyl)-acetic acid ethyl ester (45c) was prepared as described in Example 13. N-(2-Chloro-4-sulfamoyl-phenyl)-2-[4-(4-cyano-2-methyl-phenoxy)-2,3-dimethyl-phenyl]-acetamide (I-25) was prepared starting with 45c utilizing the procedure from example 1 except in step 1, 45c was used in place of 3-bromo-4-hydroxy-phenyl)-acetic acid ethyl ester and 3-methyl-4-fluoro-benzonitrile was used in place of 3-chloro-5-fluoro-benzonitrile and in step 4, 4-amino-3-chloro-benzenesulfonamide was used in place of 4-amino-benzenesulfonamide.

N-(2-Bromo-4-sulfamoyl-phenyl)-2-[4-(4-cyano-2-methyl-phenoxy)-2,3-dimethyl-phenyl]-acetamide (I-24) was prepared by the procedure described for I-25 except in the final step, 4-amino-3-bromo-benzenesulfonamide was used in place of 4-amino-3-chloro-benzenesulfonamide.

2-[4-(4-Cyano-2-methyl-phenoxy)-2,3-dimethyl-phenyl]-N-(2-methyl-4-sulfamoyl-phenyl)-acetamide (I-23) was prepared by the procedure described for I-25 except in the final step, 4-amino-3-methyl-benzenesulfonamide was used in place of 4-amino-3-chloro-benzenesulfonamide.

EXAMPLE 14

2-[4-(3,5-Dicyano-phenoxy)-3-methyl-phenyl]-N-(4-sulfamoyl-phenyl)-acetamide (I-4)

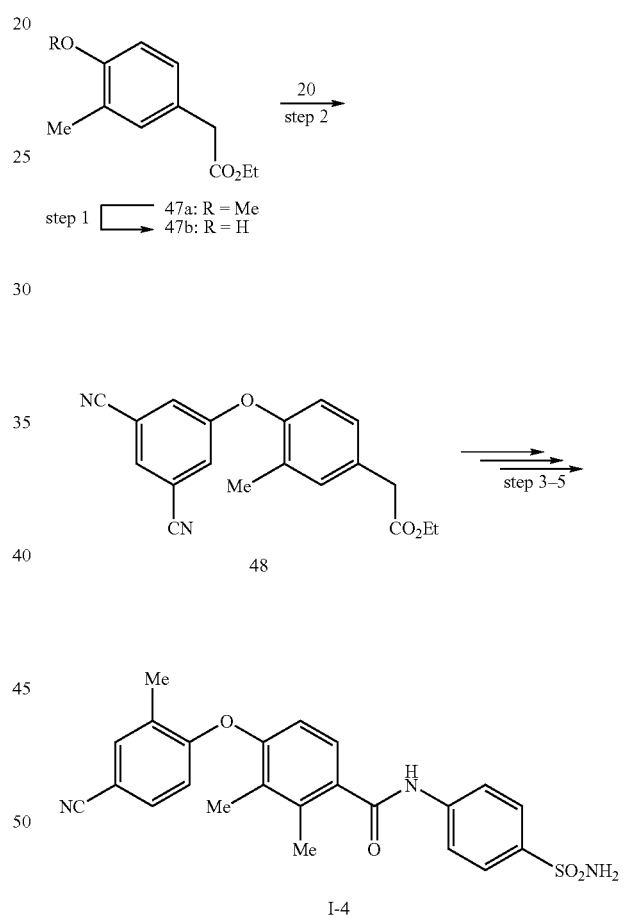

step 1—To a solution of (4-methoxy-3-methyl-phenyl)-acetic acid (47a, 2.23 g, 12.4 mmol) in DCM (15 mL) cooled at −78° C. was added dropwise via syringe $BBr_3$ (1M solution in $CH_2Cl_2$, 61.7 mmol). The reaction was stirred 1 h at −78° C. and 4 h at RT. The reaction mixture was re-cooled to −78° C. and the reaction quenched by addition of water. The solution was warmed to RT and extracted 3 times with EtOAc. The combined extracts were dried ($Na_2SO_4$), filtered and evaporated in vacuo to afford 47b.

Steps 2-5 were carried out as described for steps 1-4 of example 1 except in step 5, 48 was used in place of 17a.

EXAMPLE 15

2-[3-Bromo-4-(3-chloro-5-cyano-phenoxy)-phenyl]-N-(2-bromo-4-pentanoylsulfamoyl-phenyl)-acetamide (49c)

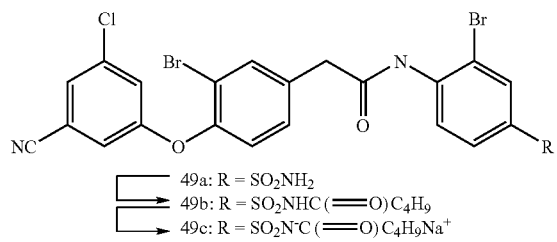

49a: R = SO$_2$NH$_2$
49b: R = SO$_2$NHC(═O)C$_4$H$_9$
49c: R = SO$_2$N$^-$C(═O)C$_4$H$_9$Na$^+$

To a solution of the sulfonamide 49a (0.188 g, 0.314 mmol), THF (2 mL) and DCE (2 mL) is added valeric anhydride (0.064 g, 0.345 mmol). A single crystal of DMAP is added to the solution. The solution is stirred for 24 h and is partitioned between water and DCM. The organic phase is washed sequentially with 10% HCl, water and brine. The organic phase is dried (Na$_2$SO$_4$) and the solvents are removed in vacuo. The residue is triturated with Et$_2$O and the resulting solid is filtered and dried to afford 49b. The acyl sulfonamide 49b is suspended in THF and is stirred until the solution is homogenous. To the solution cooled to 0° C. is added 1 equivalent of 1 M NaOH. The reaction is stirred for 10 min then is allowed to warm to RT and the solvents are removed in vacuo. The resulting material is triturated with Et$_2$O and EtOAc to afford 49c as a crystalline solid which was dried at 100° C. for 24 h.

EXAMPLE 16

HIV Reverse Transcriptase Assay: Inhibitor IC$_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 µL. The assay constituents were 50 mM Tris/HCl, 50 mM NaCl, 1 mM EDTA, 6 mM MgCl$_2$, 5 µM dTTP, 0.15 µCi [$^3$H] dTTP, 5 µg/ml poly (rA) pre annealed to 2.5 µg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 µl ice cold 20% TCA and allowed to precipitate at 4° C. for 30 min. The precipitates were collected by applying vacuum to the plate and sequentially washing with 3×200 µl of 10% TCA and 2×200 µl 70% ethanol. Finally, the plates were dried and radioactivity counted in a Packard Top-Counter after the addition of 25 µl scintillation fluid per well. IC$_{50}$'s were calculated by plotting % inhibition versus log$_{10}$ inhibitor concentrations.

EXAMPLE 17

Anti-Viral Assay

Anti-viral assays were carried out by the method described by R. E. Pauwels et al. *J. Virol. Methods* 1988 20(4):309-322.

TABLE 2

| Compound # | Anti-Viral Assay |
|---|---|
| I-61 | 0.004 |
| I-24 | 0.0026 |

EXAMPLE 18

Pharmaceutical Compositions

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of formula I

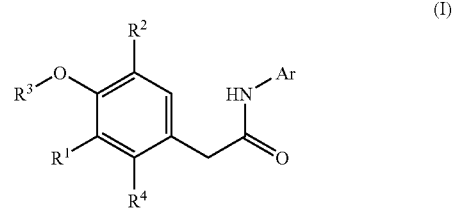

wherein:
- $R^1$ is halogen, $C_{1-6}$ alkyl, $C_{1-6}$ alkoxy, nitro or amino;
- $R^2$ is hydrogen or fluorine
- $R^3$ is phenyl substituted with one to three substituents independently selected from the group consisting of $C_{1-6}$ alkyl, $C_{1-6}$ haloalkyl, $C_{3-8}$ cycloalkyl, halogen, cyano and nitro;
- $R^4$ is hydrogen, $C_{1-6}$ alkyl or halogen;
- Ar is a substituted phenyl ring according to formula IIa with the proviso that $R^{7a}$ and $R^{7c}$ are not both hydrogen or if $R^{7c}$ is hydrogen then $R^{7a}$ is halogen, $C_{1-6}$ haloalkyl, $C_{1-6}$ alkoxy, cyano or $C_{1-6}$ alkyl wherein:

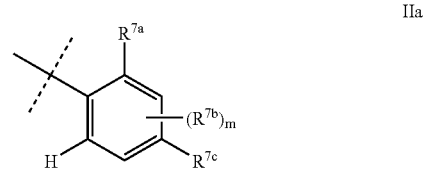

- $R^{7a}$ is selected from the group consisting of hydrogen, $C_{1-6}$ alkyl, $C_{1-3}$ haloalkyl, $C_{3-7}$ cycloalkyl, $C_{1-6}$ alkoxy, $C_{1-6}$ haloalkoxy, halogen and cyano;
- $R^{7c}$ is selected from the group consisting of hydrogen, —S(O)$_2$NR$^8$R$^9$, —X$^2$CH$_2$(CH$_2$)$_p$S(O)$_2$NR$^8$R$^9$; —X$^4$(CH$_2$)$_v$COOR$^{10}$, —X$^4$(CH$_2$)$_v$CN, —OR$^{13}$, —CO$_2$R$^{11}$, —CN, —CONR$^{8a}$R$^{9a}$ and X$^4$(CH$_2$)$_v$CONR$^{8a}$R$^{9a}$;
- $R^{7b}$ in each incidence is independently selected from the group consisting of $C_{1-6}$ alkyl; $C_{1-6}$ haloalkyl, $C_{1-6}$ alkoxy, $C_{1-6}$ alkylthio, $C_{1-6}$ alkylsulfinyl, $C_{1-6}$ sulfonyl, amino $C_{1-6}$ alkylsulfonyl, SO$_2$NR$^{11a}$R$^{11b}$, $C_{1-6}$ haloalkoxy, $C_{1-6}$ haloalkylthio, halogen, hydroxy, amino, $C_{1-6}$ alkylamino, $C_{1-6}$ dialkylamino, aminoacyl, acyl, CONR$^8$R$^9$, nitro, cyano and $C_{1-6}$ heteroalkoxy;
- $R^8$ and $R^9$ (i) taken independently, one of $R^8$ and $R^9$ is hydrogen or $C_{1-6}$ alkyl and the other of $R^8$ and $R^9$ is selected from the group consisting of hydrogen, $C_{1-6}$ alkyl, —C(=O)R$^{12}$, —(CH$_2$)$_2$N[(CH$_2$)$_2$]$_2$X$^3$ or —(CH$_2$)$_2$NR$^{11a}$R$^{11b}$; or, (ii) R$^8$ and R$^9$ taken together are (CH$_2$)$_2$—X$^3$—(CH$_2$)$_2$ or —(CH$_2$)$_o$— wherein the —(CH$_2$)$_o$— moiety is optionally substituted with one or two substituents selected from the group consisting of halogen, hydroxyl and NR$^{11a}$R$^{11b}$;

$R^{8a}$ and $R^{9a}$ (i) taken independently, one of $R^8$ and $R^9$ is hydrogen or $C_{1-6}$ alkyl and the other of $R^8$ and $R^9$ is selected from the group consisting of hydrogen, $C_{1-6}$ hydroxyalkyl, —$(CH_2)_vN[(CH_2)_2]_2X^3$ and —$(CH_2)_v$ $NR^{11a}R^{11b}$ or, (ii) $R^{8a}$ and $R^{9a}$ taken together with the nitrogen to which they are attached are pyrrolidine, piperidine said pyrrolidine or said piperidine optionally substituted with a hydroxyl or (iii) $R^{8a}$ and $R^{9a}$ taken together are $(CH_2)_2$—$X^3$—$(CH_2)_2$;

$R^{10}$ is $C_{1-6}$ alkyl;

$R^{11}$ is hydrogen or $C_{1-6}$ alkyl;

$R^{11a}$ and $R^{11b}$ are independently $R^{11}$;

$R^{12}$ is $C_{1-10}$ alkyl, —$(CH_2)_sNHR^{11a}R^{11b}$, —$(CH_2)_sOR^{11}$, —$CH_2CH(OH)CH_3$, —$CH_2N[(CH_2)_2]_2O$, —$(CH_2)_2CO_2R^{11}$, optionally substituted phenyl or pyridinyl;

$R^{13}$ is hydrogen or $C_{1-6}$ alkyl;

$X^2$ is —O— or a bond;

$X^3$ is —O—, —$S(O)_n$— or $NR^{11}$;

$X^4$ is O— or —$S(O)_n$—;

m and n are independently integers from 0 to 2;

o is an integer from 4 to 6;

p is an integer from 0 to 6;

s is an integer from 1 to 2;

v is an integer from 1 to 6; and, hydrates, solvates, and pharmaceutically acceptable salts thereof.

2. A compound according to claim 1 wherein $R^{7a}$ is hydrogen, $C_{1-6}$ alkyl, $C_{1-6}$ alkoxy, cyano or halogen;

either m=0 or m=1 and $R^{7b}C_{1-6}$ alkyl;

$R^{7c}$ is selected from the group consisting of hydrogen, —$S(O)_2NR^8R^9$, —$X^2CH_2(CH_2)_pS(O)_2NR^8R^9$, —$X^4(CH_2)_vCOOR^{10}$, —$X^4(CH_2)_vCONR^8R^9$, —$X^4(CH_2)_v COOR^{10}$, —$X^4(CH_2)_vCN$, $C_{1-6}$ alkoxy, cyano, —$CO_2R^{11}$ with the proviso that both $R^{7a}$ and $R^{7c}$ are not both hydrogen.

3. A compound according to claim 2 wherein:

$R^4$ is hydrogen or $C_{1-6}$ alkyl;

$R^1$ is chloro, bromo, $C_{1-6}$ alkyl or $C_{1-6}$ alkoxy; and, $R^2$ is hydrogen or fluoro.

4. A compound according to claim 2 wherein:

$R^{7a}$ is hydrogen, $C_{1-6}$ alkyl or halogen, m is zero;

$R^{7c}$ is selected from the group consisting of —$S(O)_2 NR^8R^9$, —$X^2CH_2(CH_2)_pS(O)_2NR^8R^9$ and —$X^4(CH_2)_v COOR^{10}$; and, $R^8$ and $R^9$ both are hydrogen.

5. A compound according to claim 4 wherein:

$R^1$ is chloro, bromo, $C_{1-6}$ alkyl or $C_{1-6}$ alkoxy; and, $R^2$ is hydrogen or fluoro.

6. A compound according to claim 5 wherein $R^3$ is phenyl independently substituted in each occurrence with one to three groups selected from the group consisting of halogen, cyano, $C_{1-6}$ haloalkyl and cyclopropyl.

7. A compound according to claim 6 wherein $R^3$ is a disubstituted phenyl.

8. A compound according to claim 7 wherein $R^3$ is a 3,5-disubstituted or a 2,5-disubstituted phenyl.

9. A compound according to claim 6 wherein $R^3$ is a 2,3,5-trisubstituted phenyl.

10. A compound according to claim 6 wherein:

$R^{7a}$ is hydrogen, $C_{1-6}$ alkyl or halogen; and, $R^{7c}$ is —$S(O)_2NR^8R^9$.

11. A compound according to claim 10 wherein $R^3$ is a 3,5-disubstituted or a 2,5-disubstituted phenyl.

12. A compound according to claim 11 wherein $R^3$ is a 2,3,5-trisubstituted phenyl.

13. A compound according to claim 1 wherein:

$R^{7a}$ is hydrogen, $C_{1-6}$ alkyl, $C_{1-6}$ alkoxy, cyano or halogen;

$R^{7c}$ is $CONR^{8a}R^{8b}$; and, at least one of $R^{8a}$ and $R^{8b}$ is other than hydrogen.

14. A pharmaceutical composition comprising a compound according to claim 1 admixed with at least one carrier, excipient or diluent.

15. A pharmaceutical composition comprising a compound according to claim 4 admixed with at least one carrier, excipient or diluent.

* * * * *